US011957793B2

(12) United States Patent
Schmid et al.

(10) Patent No.: US 11,957,793 B2
(45) Date of Patent: Apr. 16, 2024

(54) NANOPARTICLES

(71) Applicant: SINTEF TTO AS, Trondheim (NO)

(72) Inventors: Ruth Schmid, Tiller (NO); Peter Molesworth, Trondheim (NO); Yrr Mørch, Trondheim (NO); Einar Sulheim, Trondheim (NO); Heidi Johnsen, Trondheim (NO)

(73) Assignee: SINTEF TTO AS, Trondheim (NO)

( * ) Notice: Subject to any disclaimer, the term of this patent is extended or adjusted under 35 U.S.C. 154(b) by 508 days.

(21) Appl. No.: 17/270,160

(22) PCT Filed: Aug. 23, 2019

(86) PCT No.: PCT/EP2019/072612
§ 371 (c)(1),
(2) Date: Feb. 22, 2021

(87) PCT Pub. No.: WO2020/039081
PCT Pub. Date: Feb. 27, 2020

(65) Prior Publication Data
US 2021/0236435 A1    Aug. 5, 2021

(30) Foreign Application Priority Data

Aug. 23, 2018 (NO) .................................. 20181107

(51) Int. Cl.
*A61K 9/51*   (2006.01)
*A61K 45/06*  (2006.01)
*B82Y 5/00*   (2011.01)

(52) U.S. Cl.
CPC .......... *A61K 9/5138* (2013.01); *A61K 9/5192* (2013.01); *A61K 45/06* (2013.01); *B82Y 5/00* (2013.01)

(58) Field of Classification Search
CPC .... A61K 9/5138; A61K 9/5192; A61K 45/06; B82Y 5/00
See application file for complete search history.

(56) References Cited

U.S. PATENT DOCUMENTS

| | | | |
|---|---|---|---|
| 5,530,037 A | 6/1996 | McDonnell et al. | |
| 5,981,621 A | 11/1999 | Clark et al. | |
| 6,605,667 B1 | 8/2003 | Badejo et al. | |
| 2001/0010824 A1 | 8/2001 | Handjani et al. | |
| 2002/0034474 A1 | 3/2002 | Sabel et al. | |
| 2005/0042196 A1 | 2/2005 | Askill et al. | |
| 2005/0196376 A1 | 9/2005 | Loomis | |
| 2008/0138418 A1 | 6/2008 | Lee et al. | |
| 2008/0182776 A1 | 7/2008 | Lee et al. | |
| 2009/0297613 A1 | 12/2009 | Ringe et al. | |
| 2010/0015165 A1 | 1/2010 | Landfester et al. | |
| 2012/0203021 A1 | 8/2012 | Friese et al. | |
| 2019/0298682 A1* | 10/2019 | Morch | A61P 35/04 |

FOREIGN PATENT DOCUMENTS

| | | |
|---|---|---|
| WO | 2014191502 A1 | 12/2014 |
| WO | 2018148453 A1 | 2/2018 |

OTHER PUBLICATIONS

International Search Report and Written Opinion for International Application PCT/EP2019/072612; International Filing Date: Aug. 23, 2019; dated Dec. 19, 2019; 9 pages.
Chaudhari, K. et al.; "Targeting Efficiency and Biodistribution of Zoledronate Conjugated Docetaxel Loaded Pegylated PBCA Nanoparticles for Bone Metastisis"; Advanced Function Material, vol. 22, Issue No. 19; 2012; pp. 4101-4114.
Dushkin, C. et al.; "Recent Advances in the Preparation of Drug-Loaded Poly(Alkyl Cyanoacrylate) Colloidal Particles for Cancer Treatment: Nanoprecipiatation vs. Polymerization"; Nanoscience & Nanotechnology, vol. 11; 2011; pp. 186-190.
Johnsen, H. et al; "Antibody Coated Poly(alkyl cyanoacrylate) Nanocapsules for Future Medication"; Presented at Nanomat Conference, Lillehammer; 2009; 16 pages.
Landfester, K. et al.; "Formulation and Stability Mechnisms of Polymerizable Miniemulsions"; Macromolecules, vol. 32, Issue No. 16; 1999; pp. 5222-5228.
Landfester, K.; "Polyreactions in Miniemulsions"; Molecular Rapid Communications, vol. 22, Issue No. 12; 2001; pp. 896-936.
Nicolas, J. et al.; "Synthesis of poly(alkyl cyanoacrylate)-based colloidal nanomedicines"; Wiley Interdisciplinary Reviews: Nanomedicines and Nanobiotechnology, vol. 1, Issue No. 1; 2009; pp. 111-127.
Norwegian Search Report for Norwegian Application No. 20181107; Norwegian Filing Date: Aug. 23, 2018; dated Feb. 18, 2019; 3 pages.
Stolnik, S. et al.; "Long circulating microparticulate drug carriers"; Advanced Drug Delivery Reviews, vol. 16, Issues No. 2-3; 1995; pp. 195-214.
Storm, G. et al.; "Surface modification of nanoparticles to oppose uptake by the mononuclear phagocyte system"; Advanced Drug Delivery Reviews, vol. 17, Issue No. 1; 1995; pp. 31-48.
Ugelstad, J. et al.; "Emulsion Polymerization: Initiation of Polymerization in Monomer Droplets"; Journal of Polymer Science: Polymer Letters Edition, vol. 11, Issue No. 8; 1973; pp. 503-513.
Wu, M. et al.; "Well-Defined Poly(butyl cyanoacrylate) Nanoparticles via Miniemulsion Polymerization"; Macromolecular Symposia, vol. 281, Issue No. 1; 2009; pp. 39-46.

(Continued)

*Primary Examiner* — Robert A Wax
*Assistant Examiner* — John Seungjai Kwon
(74) *Attorney, Agent, or Firm* — Karen A. LeCuyer

(57) ABSTRACT

The present invention provides a nanoparticle comprising a poly(alkyl cyanoacrylate) homopolymer, or copolymer, at least one active agent and an anionic and radical inhibitor, wherein the anionic and radical inhibitor is a compound having the following formula: wherein R1 is H; and R3, R4, R5, R6 and R7 are independently selected from the group consisting of —H, —OH, C1-C6 alkoxide, C1-C6 alkyl, halides, carboxylic acid, ketone or aldehyde; wherein the anionic and radical inhibitor is present in an amount of 0.001 to 15 wt %, as well as a process suitable for manufacture of the nanoparticle.

17 Claims, 4 Drawing Sheets

(56) References Cited

OTHER PUBLICATIONS

Yoshikawa, N. et al.; "Direct Catalytic Asymmetric Aldol Reaction"; Journal of the American Chemical Society, vol. 121, Issue No. 17; 1999; pp. 4168-4178.

* cited by examiner

NANOPARTICLES

CROSS REFERENCE TO RELATED APPLICATIONS

This application is a National Stage application of PCT/EP2019/072612, filed Aug. 23, 2019, which claims the benefit of priority to Norwegian Patent Application No. 20181107, filed Aug. 23, 2018, both of which are incorporated by reference in their entirety herein.

TECHNICAL FIELD

This invention relates to poly(alkyl cyanoacrylate) nanoparticles and a process for manufacturing said nanoparticles.

BACKGROUND

The use of nanoencapsulation offers exciting possibilities in many markets, where volatile, sensitive, or harmful materials/compounds need to be protected/hidden/masked/separated and delivered/co-delivered to a desired target. This is of particular importance in the rapidly developing field of nanomedicine.

Two areas in which the use of nanoparticles has begun to demonstrate particular value are drug delivery and molecular imaging. However, in addition to medicinal applications, nanoparticles may also be highly advantageous in nanoencapsulation of various materials/compounds, such as aroma compounds, fragrances, flavours, dyes, nutraceuticals, herbicides and pesticides.

Nanoparticles for the delivery of therapeutic agents have the potential to circumvent many challenges associated with traditional delivery approaches, including lack of patient compliance to prescribed therapy, adverse side effects and poor clinical efficacy due to lack of targeted delivery and suboptimal biodistribution. Important technological advantages of nanoparticles for drug delivery include the ability to deliver water-insoluble and unstable drugs, incorporation of both hydrophobic and hydrophilic therapeutic agents and the ability to utilise various routes of administration. Nanoparticle delivery systems may also facilitate targeted drug delivery and controlled release applications, enhancing drug bioavailability at the site of action, reducing dosing frequency and overall dosage size, thereby minimising side effects. As a result of these potential advantages, a variety of nanoparticulate systems have been investigated for use as drug delivery vehicles. These include polymeric micelles, polymers, polymeric particles, liposomes, low-density lipoproteins, solid-lipid nanoparticles, dendrimers, hydrophilic drug-polymer complexes and ceramic nanoparticles.

Nanoparticle-based imaging agents may have increased circulation time and altered water-solubility, thereby avoiding rapid clearance. Many of the particulate imaging systems used to date are designed exclusively for blood pool and lymphatic system imaging. The use of targeting imaging systems has the potential to increase accumulation at the target site, leading to a higher sensitivity and thus enabling molecular imaging outside the blood pool and lymphatic system. It is envisaged that targeted nanoparticles which contain both therapeutic and imaging agents could enable the use of a single vehicle for diagnosis, treatment and follow-up monitoring of a disease.

Polymeric nanoparticles have received a great deal of attention in the field of medicine, in particular those comprising biodegradable polymers such as poly(lactic acid), poly(glycolic acid) and poly(alkyl cyanoacrylate), however those developed to date have limited effectiveness because of high clearance rates and their propensity to distribute through the whole body, including into healthy tissue. Controlled delivery of an active agent using nanoparticles therefore remains a challenge and there is a need for the development of biocompatible compositions capable of extended delivery of active agents which provide prolonged circulation time and increased stability compared to administration of the active agent alone.

Long circulating nanoparticles, i.e., those with enhanced stability in the circulatory system, have been investigated in this regard and contribute to addressing these issues. These types of nanoparticles have a hydrophilic shell around the nanoparticles, known as a stealth corona, which is typically provided by a hydrophilic polymer and leads to an increase in the blood circulation half-life of the nanoparticle, vastly increasing circulation times. The hydrophilic shell mimics water and acts as an immunoprotective layer, rendering the nanoparticles relatively "invisible" to the immune system, enabling them to avoid uptake by phagocytic cells. Stealth-structured nanoparticles are well known and have been prepared with a variety of nanoparticle cores and with a range of polymeric shells, as discussed in Nicolas and Couvreur in Rev. Nanomed. Nanobiotechnol., 2009, 1, 111-127, Storm et al., Adv Drug Deliv Rev 1995, 17: 31-48 and Stolnik, Illum & Davis, Adv Drug Deliv Rev 1995, 16: 195-214. Their use in the encapsulation of therapeutic agents has also been described in, for example, US 2002/0034474. A commercially available example is Doxil®, which comprises pegylated liposomes containing doxorubicin.

Many methods for preparing nanoparticles are known, such as emulsion polymerisation, self-assembly and nano-precipitation. Anionic emulsion polymerisation is described in, for example, US 2008/0138418.

Miniemulsion processes are known for the production of nanoparticles with average sizes typically in the range 1-1000 nm, most typically 50-500 nm as disclosed e.g., in Landfester in Macromol. Rapid Comm. 2001, 22, 896-936 and Landfester et al in Macromolecules 1999, 32, 5222-5228. The method was first described by Ugelstad et al. (1973) Emulsion polymerization: initiation of polymerization in monomer droplets. *J Polym Sci Polym Lett Ed* 11:503-513. The miniemulsion technique for the preparation of polymeric nanoparticles is a technology by which a dispersion is prepared, by converting a stable nanoemulsion of a dispersed phase in a continuous phase into a nanoparticle dispersion by polymerisation reactions. The technology involves mixing the various components in the dispersed phase before emulsification with the continuous phase takes place, resulting in the production of an emulsion in which each droplet has an identical composition of active agent and monomers. All types of polymerisation reactions may be applied in these droplet nanoreactors. In the case of the present invention, oil-in-water miniemulsions and anionic polymerisation at the droplet interface, commonly started by adding an initiator to the continuous phase, are the preferred embodiments. The particles formed are typically identical or almost identical to the droplets from which they are prepared, in terms of size and size distribution, resulting in high reproducibility of the process.

Miniemulsions are usually stabilised by a surfactant and a co-stabiliser, the latter often referred to as "hydrophobe". The co-stabiliser contributes to the osmotic stabilisation of the emulsion by increasing the osmotic pressure, which counteracts the capillary or Kelvin pressure due to surface tension of the droplets and reduces Ostwald ripening by minimising diffusion of the monomer from small to large droplets.

In conventional emulsion polymerization, the ingredients are comprised of water, a monomer of low water solubility, water-soluble initiator and a surfactant. If the surfactant concentration is below the critical micelle concentration, particles are formed by precipitation and agglomeration of growing polymer chains that become insoluble in the continuous phase. If the surfactant concentration is above the critical micelle concentration, monomers diffuse into surfactant micelles followed by initiation and polymerization. The process involves large monomer droplets (1-10 µm) that are the reservoir for the monomer. On the other hand, miniemulsions consist of small, stable, and narrowly distributed monomer droplets in a continuous phase. The system is obtained by high shear; for example, by ultrasonication or high-pressure homogenizers. The high stability of the droplets is ensured by the combination of the water-soluble amphiphilic component (the surfactant) and the co-stabilizer, which is soluble in the monomer and homogeneously distributed in the droplet phase. These small droplets can then act as nanocontainers in which polymerizations can take place, either inside the droplets or at the interface of the droplets, resulting in the formation of nanoparticles. In emulsion polymerization, encapsulation of active ingredients that must be dissolved in the water phase relies on inclusion during the formation of the aggregates, resulting in loading amounts typically in the range of 1% or less (C. Dushkin & G. Yordanov, *Nanoscience & Nanotechnology*, 11, 186 (2011): "Recent advances in the preparation of drug-loaded poly(alkyl cyanoacrylate) colloidal particles for cancer treatment: nanoprecipitation vs. polymerization), while in miniemulsion polymerisation processes, where the active ingredient is dissolved in the monomer before the emulsion is formed, it can reach amounts of 5-50% of the droplets, dependent on the material, resulting in corresponding loading amounts of 5-50% in the final nanoparticles. Conventional emulsion processes result in nanospheres, which are matrix systems, where the drug is physically dispersed in the polymer, while miniemulsion processes may be combined with interfacial polymerisation reactions resulting in nanocapsules, which are vesicular systems in which the drug is solubilized in a liquid core, surrounded by a thin polymer layer. It should therefore be appreciated that conventional emulsions and miniemulsion processes are quite different and the products produced therefrom are structurally distinct.

In US 2008/182776 and US 2010/015165 miniemulsion polymerisation processes for the preparation of poly(alkyl cyanoacrylate) nanoparticles are described. The polymerisation initiators used are surfactants (pluronics) and primary or secondary amines, respectively, although, in general, any nucleophilic compound, containing for example hydroxyl or amino groups may be used. Examples of initiators include sodium hydroxide, amino acids (e.g., glycine) and polyethylene glycols. Initiation may also take place via alteration of the pH as discussed in, for example, US 2009/0297613.

An advantageous process for preparing poly(alkyl cyanoacrylate) nanoparticles is also described in WO 2014/191502.

As discussed above, the production of poly(alkyl cyanoacrylate) nanoparticles by the miniemulsion process offers a number of advantages. However, the alkyl cyanoacrylate monomers are very reactive and polymerise very easily in the presence of radical and/or anionic initiators. A side effect of the reactivity of alkyl cyanoacrylate monomers is that they are vulnerable to premature polymerisation (either anionic or radically initiated) caused by structural features of the active ingredient/agent. The structural features include for instance $M-NH_3$ (wherein M is a metal, i.e. a metal-ammonia complex), $R-NH_2$, $R_1R_2-NH$, $R_1R_2R_3N$, $R_1=NR_2$, $R-OH$, $R-Cl$, $R-Br$, $R-I$, $R-SH$, $RiN=NR_2$, $R-NHOH$, structurally associated $H_2O$ and enols. This premature polymerisation severely limits the range of active ingredients that can be dissolved into ACA monomers prior to polymerisation and has significantly reduced the potential of such nanoparticles in many fields. To avoid premature polymerisation of the alkyl cyanoacrylate during the miniemulsion polymerisation it is known to add an anionic or radical inhibitor, such as methane sulphonic acid (MSA, anionic inhibitor) and butylated hydroxytoluene (BHT, radical inhibitor). MSA and other acid inhibitors prevent polymerisation of the ACA by adjusting the pH of the polymer droplet and preventing the formation of anions that trigger polymerisation. This is achieved either by neutralisation of an anion (via donation of a proton) to a neutral molecule, or formation of a cation (via donation of a proton) thus preventing nucleophilic attack by a lone pair of electrons (e.g., on nitrogen). The known inhibitors do however have various disadvantages. For instance, MSA is a strong acid that may decompose acid labile compounds (for instance active pharmaceutical ingredients, i.e., API's) while neither MSA nor BHT are suitable for use in a clinical setting due to their toxicity. Further, radical inhibitors alone are not efficient enough to totally hinder premature polymerisation when the miniemulsion process is used to nanoencapsulate reactive compounds and API's which may act as radical and/or anionic initiators.

The purpose of the present invention is to provide improved poly(alkyl cyanoacrylate) nanoparticles suitable for use in a clinical setting and a process for manufacturing such nanoparticles.

SUMMARY OF THE INVENTION

The present invention is defined by the attached patent claims. Further optional features of the present invention and definition of terms are disclosed in the detailed description below.

In a first aspect, the present invention provides a nanoparticle comprising a poly(alkyl cyanoacrylate) homopolymer, or copolymer, at least one active agent and an anionic and radical inhibitor, wherein
the anionic and radical inhibitor is a compound having the following formula:

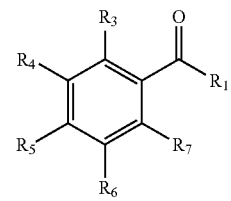

wherein
$R_1$ is H; and
$R_3$, $R_4$, $R_5$, $R_6$ and $R_7$ are independently selected from the group consisting of —H, —OH, $C_1$-$C_6$ alkoxide, $C_1$-$C_6$ alkyl, halides, carboxylic acid, ketone or aldehyde; wherein the anionic and radical inhibitor is present in an amount of 0.001 to 15 wt %.

A nanoparticle comprising a poly(alkyl cyanoacrylate) homopolymer, or copolymer, may also be termed a poly(alkyl cyanoacrylate) nanoparticle.

In an embodiment of the nanoparticle, the anionic and radical inhibitor is present in an amount of 0.01 to 10 wt %, 0.01 to 5 wt % or 0.01 to 2 wt %.

In an embodiment of the nanoparticle, the active agent is a compound having a functional group selected from the group consisting of M-$NH_3$ (wherein M is a metal), R—$NH_2$, $R_1R_2$—NH, $R_1R_2R_3$N, $R_1$=$NR_2$, R—OH, R—$C_1$, R—Br, R—I, R—SH, RiN=$NR_2$, R—NHOH, structurally associated $H_2O$ and enols.

In an embodiment, the nanoparticle is manufactured by a process according to the second aspect of the invention defined below.

In a second aspect, the present invention provides a process for the preparation of nanoparticles of a poly(alkyl cyanoacrylate) homopolymer or copolymer, comprising, in a single step, the anionic polymerisation of an oil-in-water miniemulsion, wherein said miniemulsion comprises
  (i) at least one alkyl cyanoacrylate monomer;
  (ii) at least one surfactant;
  (iii) one or more active agent;
  (iv) optionally an anionic polymerisation initiator; and
  (v) an anionic and radical inhibitor, wherein the anionic and radical inhibitor is a compound having the following formula:

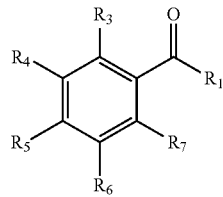

wherein
  $R_1$ is H; and
  $R_3$, $R_4$, $R_5$, $R_6$ and $R_7$ are independently selected from the group consisting of —H, —OH, $C_1$-$C_6$ alkoxide, $C_1$-$C_6$ alkyl, halides, carboxylic acid, ketone or aldehyde.

In an embodiment of the process, the anionic and radical inhibitor is a single compound able to react with any of a nucleophile and a radical.

In an embodiment of the process, the anionic and radical inhibitor is present in an amount of 0.001 to 15 wt % relative to an oil phase of the miniemulsion, or in an amount of 0.01 to 10 wt %, 0.01 to 5 wt % or 0.01 to 2 wt %. The oil phase comprises the non-aqueous components of the miniemulsion, for instance the at least one alkyl cyanoacrylate monomer.

In an embodiment of the process, the anionic and radical inhibitor has a higher affinity for radicals and nucleophiles than the at least one alkyl cyanoacrylate monomer.

In an embodiment of the process, the anionic and radical inhibitor has an octanol-water partition coefficient (log P) in the range of 1.0-3.0, preferably in the range of 1.0-2.5 or even more preferred in the range of 1.0-2.0.

In an embodiment of the process, the anionic and radical inhibitor is selected from the group consisting of 4-hydroxy-3,5-dimethylbenzaldehyde, 4-hydroxy-3,5-dimethoxybenzaldehyde, vanillin, salicylaldehyde and benzaldehyde.

In an embodiment of the process, the active agent is a therapeutic agent or an imaging agent. In further embodiments, the active agent may be selected from the group comprising aroma compounds, flavours, fragrances, dyes, nutraceuticals, herbicides and pesticides.

In an embodiment of the process, the at least one surfactant is at least one polyalkylene glycol selected from the group consisting of polyethylene glycols (PEG) and polypropylene glycols (PPG) or mixtures thereof.

In an embodiment of the process, the at least one surfactant initiates the anionic polymerisation reaction.

In an embodiment of the process, the at least one surfactant in step (ii) comprises at least two polyalkylene glycols selected from the group consisting of polyethylene glycols (PEG) and polypropylene glycols (PPG) or mixtures thereof.

In an embodiment of the process, the active agent comprises a functional group selected from the group consisting of M-$NH_3$ (wherein M is a metal), R—$NH_2$, $R_1R_2$—NH, $R_1R_2R_3$N, $R_1$=$NR_2$, R—OH, R—$C_1$, R—Br, R—I, R—SH, RiN=$NR_2$, R—NHOH, structurally associated $H_2O$ and enols.

In an embodiment of the process, the miniemulsion may comprise an anionic polymerisation initiator, i.e., an initiator able to start the anionic polymerization of the at least one alkyl cyanoacrylate monomer. Preferably, the anionic polymerisation reaction is initiated by the at least one surfactant.

In an embodiment of the process, the manufactured nanoparticle is a nanoparticle according to the first aspect of the invention.

In an embodiment, the process does not comprise a step of centrifugation.

In a third aspect, the present invention provides a pharmaceutical composition comprising a nanoparticle according to the first aspect, or a nanoparticle obtained by the process according to the second aspect, and one or more pharmaceutically acceptable carriers, diluents or excipients.

In a fourth aspect the present invention provides a nanoparticle according to the first aspect, or a nanoparticle obtained by the process according to the second aspect, for use in medicine, preferably for use in drug delivery or molecular imaging.

In a fifth aspect, the present invention provides a nanoparticle according to the first aspect, or a nanoparticle obtained by the process according to the second aspect, for the use in agriculture, aquaculture, antibacterial applications, nutraceuticals, food/feed applications, cosmetics, self-healing, household applications and body care.

The term "an anionic and radical inhibitor" is in the present description intended to define a single compound able to inhibit both undesired anionic and undesired radical initialised polymerisation.

DETAILED DESCRIPTION OF THE INVENTION

Figures 1A, 1B, 1C, 1D:
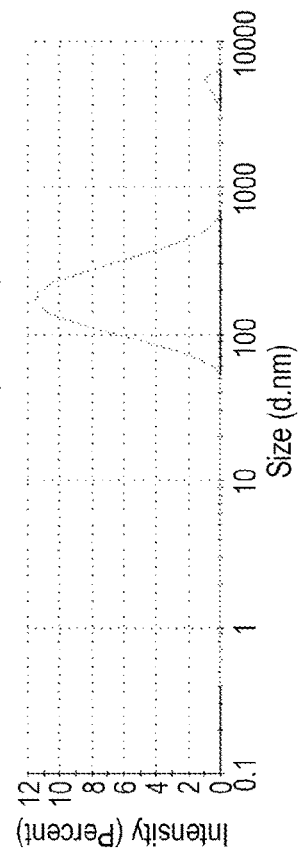
FIGS. 1A-1M show particle size by distribution plots from selected examples, before and after centrifugation.

The present invention provides poly(alkyl cyanoacrylate) nanoparticles and a process for the preparation of such nanoparticles from a poly(alkyl cyanoacrylate) homopolymer or copolymer, wherein said process comprises, in a single step, the formation of said nanoparticles by anionic polymerisation of an oil-in-water miniemulsion.

Miniemulsion

As used herein, the term "miniemulsion" means a specific type of emulsion comprising stable droplets with typical mean sizes within the range 50 to 500 nm. The particle size is influenced by a number of factors, including the amount of surfactant present, the viscosity of the system as a whole and the shear rate used to produce the droplets. Typical particle size distribution curves (measured using, for example, dynamic light scattering) for miniemulsions are Gaussian in shape and are relatively narrow. The miniemulsions of the present invention preferably have a polydispersity index (PDI) of 0.3 or less, more preferably 0.2 or less, such as about 0.1.

Miniemulsions are ideally stabilised by the presence of a surfactant and a co-stabiliser, the latter often referred to as "hydrophobe". The co-stabiliser contributes to the osmotic stabilisation of the emulsion by increasing the osmotic pressure, which counteracts the capillary or Kelvin pressure due to surface tension of the droplets and reduces Ostwald ripening. Ostwald ripening refers to the process by which molecules diffuse from small droplets to large ones through the continuous phase. This process disrupts the emulsion structure. Miniemulsions may be direct (oil-in-water) or inverse (water-in-oil) although for the purposes of the present invention, the term "miniemulsion" may be considered to refer only to direct miniemulsions. In the miniemulsions of the invention therefore, water forms the continuous phase. The oil phase typically contains the monomers used in the anionic polymerisation, the co-stabiliser and the active agent, if present.

As discussed above, miniemulsions and miniemulsion polymerisation for the preparation of nanoparticles are known in the art.

The miniemulsion may be prepared by any known method in the art, such as that described in US 2009/0297613. Processes typically involve forming the oil and water phases, mixing these and subjecting the mixture to high shear forces, e.g., ultrasonication or homogenisation, to form a stable emulsion of oil droplets containing the monomer with a stabiliser/surfactant on the surface, and then subsequently adding a hydrophilic initiator. Polymerisation of the monomer droplets then occurs by initiation at the droplet interface to form polymeric particles which have the same size as the droplets before polymerisation. The hydrophilic initiator is attached to the surface of the particles. Alternatively, polymerisation is initiated by adjustment of the pH. It should be apparent to the skilled worker that the miniemulsion polymerisation processes described in the context of the present invention are quite distinct from emulsion polymerisation processes whereby polymeric nanoparticles are formed directly from a solution of the monomers in a solvent and from emulsion processes using premade polymers, whereby the polymeric nanoparticles are formed by self-assembly of these pre-made polymers.

The miniemulsions of the present invention comprise at least three components: polymerizable monomers comprising at least one alkyl cyanoacrylate monomer; at least one surfactant, preferably a polyalkylene glycol selected from polyethylene glycols (PEGs) and polypropylene glycols (PPGs), or mixtures thereof, and an anionic and radical inhibitor. The miniemulsions may also optionally comprise one or more active agents. In one embodiment of the invention, at least one of said surfactants, e.g., at least one polyalkylene glycol, initiates the anionic polymerisation of the polymerisable monomers.

The use of an anionic and radical inhibitor as described below is a key feature of the present invention and provides several advantageous effects.

Anionic and Radical Inhibitors

The anionic and radical inhibitor used in the present invention preferably comprises 0.001 to 15 wt % relative to an oil phase of the miniemulsion, or in an amount of 0.01 to 10 wt %, 0.01 to 5 wt % or 0.01 to 2 wt %.

Any compound/molecule able to inhibit both anionic and radical polymerisation may be used as an anionic and radical inhibitor, provided the inhibitor is oil soluble and non-toxic (i.e., suitable for clinical use).

To hinder radical polymerisation the compound must be able to readily accept a radical, preferential to the monomer and prevent the propagation of said radical. Ideally the compound should react sacrificially, and irreversibly in such a fashion that the radical is not further propagated.

In a similar fashion, to act as an anionic inhibitor, the compound must be able to act as an electrophile to nucleophilic attack from, but not limited to hydroxyl ions in water, hydroxyl groups, carbanions, oxygen, nitrogen, halogen and sulfur anions. Ideally the compound should react irreversibly and in such a fashion that further propagation of the anion is prevented. The anionic and radical inhibitors selected for use herein are known to act as electrophiles (e.g., in the aldol reaction, ref. Yoshikawa et al., Direct Catalytic Asymmetric Aldol Reaction, *J. Am. Chem. Soc.* 1999, 121, 4168-4178), without acting as an acid (e.g. a proton donor) and as such behave different mechanistically from known anionic polymerisation inhibitors such as MSA and other organic acids. Similarly, the selected compounds can accept a radical inhibitor and, whilst they share many features similar to common antioxidants/radical inhibitors, are not typically applied in this role.

In other words, the anionic and radical inhibitor may preferably have a higher affinity for radicals and nucleophiles than the at least one alkyl cyanoacrylate monomer. The skilled person may easily determine whether an anionic and radical inhibitor has a higher affinity for radicals and nucleophiles than the at least one alkyl cyanoacrylate monomer. For instance, the skilled person may mix the anionic and radical inhibitor with the chosen alkyl cyanoacrylate monomer and add an active component known for readily polymerizing the monomer. The active component is a material or mixture of materials able to initiate anionic and/or radical polymerization. If no polymerization is observed, the anionic and radical inhibitor has a higher affinity for radicals and nucleophiles than the alkyl cyanoacrylate monomer.

As such, the compound may feature a functional group, or combination of functional groups, that can react with a radical, and act as an electrophile during a reaction with an anion (i.e., a nucleophile).

The functional group, or combination of functional groups includes at least one aromatic ring comprising an alfa aldehyde group. Additional functional groups may be, but not limited to, aromatic hydroxy groups, aldehydes, ketones and quinones, enones and amines. The aromatic ring may be further substituted with at least one electron donating alkyl or alkoxy group. The electron donating alkyl or alkoxy group may advantageously be sterically bulky provided the solubility in the monomer used in the miniemulsion process is sufficient. It is also preferred that the molecule is readily soluble in the oil phase of a miniemulsion process and has limited water solubility.

The anionic and radical inhibitors for use in the present invention have an octanol-water partition coefficient (log P) in the range of 1.0-3.0, preferably in the range of 1.0-2.5, and even more preferred in the range of 1.0-2.0. The disclosed log P ensures that the anionic and radical inhibitors used in the process according to the invention have an optimal distribution throughout the miniemulsion, i.e., sufficient inhibitor is present in the oil phase.

Log P can be determined by several methods, including shake flask, pH-Metric, reverse phase HPLC and electrochemical, or calculated by use of appropriate software. The log P values disclosed in the present specification and used to define the anionic and radical inhibitors of the invention were calculated by ACD/Labs log P prediction model, see table 1 below.

The anionic and radical inhibitors used in the supportive experiments below are vanillin, 4-hydroxy-3,5-dimethylbenzaldehyde, 4-hydroxy-3,5-dimethoxybenzaldehyde, salicylaldehyde, benzaldehyde, vitamin E, vitamin K3 and vitamin K1. The vitamins, MSA; BHT and BHA are included as comparative examples.

Surfactant

TABLE 1

| Inhibitor | Type | logP [theor.] |
|---|---|---|
| MSA | Anionic inhibitor | — |
| BHA | Radical inhibitor | 3,360 |
| BHT | Radical inhibitor | 5,168 |
| Vanillin | Anionic and radical inhibitor | 1,208 |
| Salicylaldehyde | Anionic and radical inhibitor | 1,580 |
| Benzaldehyde | Anionic and radical inhibitor | 1,452 |
| α-tocopherol (Vit E)[1] | Anionic (weak) and radical inhibitor | 10,724 |
| Vitamin K1 | Anionic (weak) and radical inhibitor | 10,305 |
| Vitamin K3 | Anionic (weak) and radical inhibitor | 1,988 |
| 3,5-dimethyl-4-hydroxy-benzaldehyde | Anionic and radical inhibitor | 2,434 |
| 4-hydroxy-3,5-dimethoxy-benzaldehyde | Anionic and radical inhibitor | 1,304 |

The miniemulsions of the invention may comprise at least one surfactant. Any typical surfactant known in the art may be used, however preferable surfactants include fatty acids of glycerols, sorbitol and other multifunctional alcohols, poloxamers, poloxamines, polysorbates, polyoxyethylene ethers and polyoxyethylene esters, ethoxylated triglycerides, ethoxylated phenols and diphenols, polysaccharides (e.g., hyaluronic acid and sialic acid), proteins, metal salts of fatty acids, metal salts of fatty alcohol sulfates, sodium lauryl sulfate, metal salts of sulfosuccinates and mixtures thereof. Particularly preferred surfactants include polyoxyethylene ethers and polysorbates.

The surfactant preferably comprises 0.05 to 5 wt % of the water phase of the miniemulsion, more preferably 0.1 to 2 wt %.

In addition to these components, the miniemulsion may further comprise a co-stabiliser in the oil phase. The co-stabiliser is typically highly water insoluble, i.e., has a solubility of less than $5 \times 10^{-5}$ mol/L, more preferably less than $5 \times 10^{-6}$ mol/L and still more preferably less than $5 \times 10^{-7}$ mol/L and may be any substance which is compatible with the polymerisable monomer(s), such as a hydrocarbon, silane, organosilane, fatty acid ester, oil (e.g. plant oil), hydrophobic dye or lipid. Examples of suitable co-stabilisers include hexadecane, cetyl alcohol, miglyol and olive oil. Particularly preferred co-stabilisers include miglyols and plant oils. In an alternative embodiment, the active agent may perform the role of the co-stabiliser.

The co-stabiliser preferably comprises 0.5 to 5 wt % of the oil phase of the miniemulsion, more preferably 1 to 3 wt %.

In a further embodiment the miniemulsion used in the process of the current invention comprises a crosslinker (especially a biodegradable crosslinker), preferably in the oil phase (i.e., the discontinuous phase). The crosslinker is preferably an anhydride, an acrylate or a bis-cyanoacrylate, such as mono- or polyethylene glycol dimethacrylate, methacrylic anhydride, 1,6-hexanediol bis-cyanoacrylate or methylene dimethacrylate.

The oil phase content of the miniemulsions of the invention may be up to 50%, but is typically up to 15-25 wt %, preferably up to 15 wt % or in the range of 5-15 wt %. The skilled person will understand that the oil phase content of the mini-emulsions of the present invention may also be referred to as the solid content. Thus, the terms "solid content" and "oil phase content" are interchangeable in the context of the present invention.

Polymerisable Monomers

The polymerisable monomers in the miniemulsion of the present invention comprise at least one alkyl cyanoacrylate monomer. These are biodegradable monomers whose use in the preparation of nanoparticles has been widely reported. The alkyl cyanoacrylate may be a monofunctional or difunctional acrylate i.e., containing single or multiple acrylate functionalities. Any straight or branched chain alkyl cyanoacrylate monomer or derivative thereof may be used, however preferred monomers are those of $C_1$-$C_{10}$ alkyl cyanoacrylates, more preferably $C_2$-$C_8$ alkyl cyanoacrylates. A single monomer may be used or mixtures of different alkyl cyanoacrylates may be used. Preferred alkyl cyanoacrylates include ethyl cyanoacrylate, butyl (n-butyl) cyanoacrylate, 2-ethylbutyl cyanoacrylate, n-octyl cyanoacrylate and derivatives and mixtures thereof. Butyl cyanoacrylate, 2-ethylbutyl cyanoacrylate and n-octyl cyanoacrylate are particularly preferred.

Without wishing to be bound by theory, it is believed that the nature of the monomers influences the degradation rate of the polymer. The more hydrophobic the monomer (i.e., the longer the alkyl chain), the slower the degradation rate, probably due to a lower water level in more hydrophobic polymers. It is therefore another embodiment of the invention to use a mixture of alkyl cyanoacrylates of differing chain length, e.g., one with a short alkyl chain and one with a long alkyl chain such as butyl cyanoacrylate mixed with 2-ethylbutyl cyanoacrylate or n-octyl cyanoacrylate.

In one embodiment, a cyanoacrylate homopolymer is used, i.e. formed from a single monomer.

The alkyl cyanoacrylate monomers are preferably present in an amount of 1 to 100 wt %, more preferably 75-100 wt %, even more preferably 95-100 wt % of the total amount of monomers.

In addition to the alkyl cyanoacrylate monomers, other co-monomers may also be present in the miniemulsions of the invention. It is preferable if these co-monomers are also biocompatible or biodegradable. Suitable co-monomers include, but are not limited to acrylates, vinyl esters, vinyl ethers, vinyl epoxides, cyclic siloxanes and lactones. Said co-monomers may also be crosslinkers depending on the desired particle properties.

The polymerisable monomers preferably comprise 25 to 99.5 wt % of the oil phase of the miniemulsion, more preferably 30 to 70 wt %.

Polyalkylene Glycols

Preferred surfactants for use in the present invention are polyalkylene glycols. The miniemulsions of the present invention may comprise at least one polyalkylene glycol selected from the group consisting of polyethylene glycols (PEG) and polypropylene glycols (PPG) or mixtures thereof. At least one of the polyalkylene glycols preferably initiates the anionic polymerisation reaction.

The polyalkylene glycols are usually added to the continuous phase of the miniemulsion, i.e., the water phase. One of the polyalkylene glycols may in some instances be covalently attached to a targeting moiety. It is especially preferred if the polyalkylene glycols are so water-soluble that a homogeneous solution may be prepared to add to the miniemulsion.

By the term "polyethylene glycol" (PEG) we mean any polymer containing mostly ethylene oxide repeating units, i.e. —$CH_2$—$CH_2$—O— units. Typical polyethylene glycols have a molecular mass less than 20000 g/mol, preferably less than 10000 g/mol. By the term "polypropylene glycol" (PPG) we mean any polymer containing mostly propylene oxide repeating units, i.e. —$CH_2$—$CH_2$—$CH_2$—O— units.

The polyalkylene glycols may have a hydroxy or amino end group, or a mixture thereof. The polyalkylene glycols are water soluble. By water soluble we mean that they must have a solubility in water which is high enough to enable the formation of a homogenous solution in water, which may then be added to the miniemulsion, i.e. a solubility of more than 10 g/L at room temperature and pressure (RTP).

Examples of suitable polyalkylene glycols include polyethylene glycol and polypropylene glycol homopolymers and copolymers thereof. It should be noted that the term "polyethylene glycol" is intended to cover polysorbates (e.g., polysorbate 80). Most importantly, the copolymers may be block copolymers. Examples of suitable copolymers include polypropylene glycol)-poly(ethylene glycol) block copolymers, polyalkylamine-polyalkylene glycol block copolymers, lipid-polyalkylene glycol block copolymers and polylysine-polyalkylene glycol block copolymers.

The length of the blocks of each polymer may be varied so as to alter the properties of the copolymer, with the proviso that the copolymer remains water soluble. Increasing PPG content for example, reduces water solubility. In one embodiment, there is preferably a hydroxyl or amino end group directly attached to the PPG. Preferably the end group is an amino end group.

Preferably, the ratio of polyethylene glycol units to PPG units is in the range 1:5 to 5:1, such as 1:1. Each block may contain 2-40 monomer units. It is further preferred however if polyethylene glycol units are in excess.

Typical molecular weights for the polyalkylene glycol-PPG block copolymers of the invention are lower than 20 000 g/mol, preferably lower than 10 000 g/mol, such as 1000 to 8000.

It is preferred if a polyethylene glycol is used, i.e., one in which polyethylene glycol units are present in the majority and it is preferred if that polyethylene glycol further comprises a hydrophobic component so as to optimise properties and enable efficient hydrophobic interaction with the monomers in the oil phase. Preferably the hydrophobic component is attached covalently to the polyethylene glycol, most preferably between the amino or hydroxyl end group and the rest of the polyethylene glycol moiety.

The hydrophobic component is typically an alkyl chain, polyether or a lipid. A particularly preferred hydrophobic component is polypropylene oxide (PPO) thus forming a polyethylene glycol/polypropylene glycol block copolymer. It should be understood that PPG is equivalent to PPO.

One of the at least one polyalkylene glycol(s) may in some instances be covalently attached to a targeting moiety. The targeting moiety may be any suitable moiety which targets, or causes the particle to become localised at specific locations within a subject. The targeting moiety should contain a functional group that can be reacted with the terminus opposite to the amino group terminus of the polyalkylene glycol. Suitable functional groups are those capable of forming a covalent bond with the polyalkylene glycol, such as amino, hydroxy, azide, alkyne and thio. The conjugation of the targeting moiety to the polyalkylene glycol may be performed by any method routinely used in the art, such as "click" chemistry, see for instance Kolb et al., "Click Chemistry: Diverse Chemical Function from a Few Good Reactions". Angewandte Chemie Int. Ed. 2001, 40 (11): 2004-2021.

Preferably, the targeting moiety has a molecular weight in the range 100 to 200 000 Da, more preferably 200 to 50000 Da, even more preferably 300 to 15000 Da.

It should be appreciated that a single targeting moiety or a mixture of different targeting moieties may be used.

Exemplary targeting moieties are selected from the group consisting of an amino acid, protein, miniprotein (e.g. cysteine-knot miniprotein), peptide, antibody, antibody fragments, saccharide, carbohydrate, glycan, cytokine, chemokine, nucleotide, lectin, lipid, receptor, steroid, neurotransmitter, cell surface marker, cancer antigen, glycoprotein antigen, aptamer or mixtures thereof. Preferably, the targeting moiety or mixture of targeting moieties includes linear and cyclic peptides or antibody fragments.

Preferably, the amount of polyalkylene glycol(s) (in total) is 0.05-5 wt %, more preferably 0.1-2 wt % of the water phase of the miniemulsion. The amount of polyalkylene glycol(s) (in total) should preferably not exceed 15 wt %, more preferably 10 wt %.

Active Agent

The active agent may be any agent which has a medicinal application, e.g., therapeutic agents or imaging agents, as well as any other compound of interest for nanoencapsulation, such as, but not limited to, aroma compounds, flavours, fragrances, dyes, nutraceuticals, herbicides and pesticides. The active agent may be water soluble or water insoluble, preferably water insoluble. Where the active agent is water soluble it is typically added as a fine powder in an oil or added after being converted to a water insoluble form (e.g., by acidifying a water-soluble salt form of an API into a water insoluble neutral form or by ion pairing with a water insoluble counter ion). In a preferred embodiment, the active agent comprises 1 to 75 wt % of the oil-phase of the miniemulsion, more preferably 10-30 wt %.

Exemplary therapeutic agents, which of course do not restrict the present invention, include chemotherapeutic agents, diagnostic agents, antineoplastic agents, prophylactic agents, nutraceutical agents, antibiotics, antiviral agents, antiinflammatory agents, small molecule kinase inhibitors, nucleic acids, proteins, peptides, lipids, carbohydrates, hormones, metals, ceramics, drugs, vaccines, immunological agents, and mixtures thereof.

Preferred therapeutic agents include doxorubicin, gemcitabine, daunorubicine, procarbazine, docetaxel, paclitaxel, cabazitaxel, 5-fluorouracil, mitomycin, cytarabine, etoposide, methotrexate, vinblastine, vincristine, bleomycin, cloxacillin, oxacillin, daptomycin, irinotecan, mitoxantrone, mitoxantrone hydrochloride, aldesleukin, asparaginase, busulfan, carboplatin, cladribine, camptothecin, dacarbazine, ftorafur, 5'deoxyfluorouridine, eniluracil, deoxycytidine, 5-azacytosine, 5-azadeoxycytosine, allopurinol, 2-chloroadenosine, trimetrexate, aminopterin, methylene-10-deazaaminopterin, cisplatin, oxaliplatin, picoplatin, tetraplatin, satraplatin, platinum-DACH, ormaplatin, epirubicin, etoposide phosphate, 9-aminocamptothecin, vindesine, L-phenylalanine mustard, 6-mercaptopurine, 6-thioguanine, amsacrine, karenitecin, acyclovir, valacyclovir, ganciclovir, amantadine, rimantadine, lamivudine, zidovudine, bevacizumab, trastuzumab, rituximab, sirolimus, temsirolimus, everolimus, imatinib, sorafenib, capecitabine, osimertinib, trifluridine, afatinib, trametinib, abiraterone, erlotinib, gefitinib, cyclophosphamide, sunitinib, eribulin, cabozantinib, idelalisib, tamoxifen, bortezomib, belinostat, ceritinib, lapatinib, alectinib, olaparib, fulvestrant, anostrozole, N-(4-((3-(2-aminopyrimidin-4-yl)pyridin-2-yl)oxy)phenyl)-4-(4-methylthiophen-2-yl)phthalazin-1-amine (AMG900), protein kinase D1 inhibitors, protein kinase D2 inhibitors, protein kinase D3 inhibitors, 12-(2-Cyanoethyl)-6,7,12,13-tetrahydro-13-methyl-5-oxo-5H-indolo[2,3-a]pyrrolo[3,4-c]carbazole (Gö6976), N-[2-(p-Bromocinnamylamino)ethyl]-5-isoquinolinesulfonamide (H89) and combinations thereof.

Particularly preferable therapeutic agents are docetaxel, cyclophosphamide, everolimus, capecitabine, bortezomib, belinostat, cabazitaxel, paclitaxel, 5-fluorouracil, cloxacillin, oxacillin, daptomycin.

Other highly preferable therapeutic agents include carboplatin, oxaliplatin, picoplatin, tetraplatin, satraplatin, cisplatin, platinum-DACH and ormaplatin.

Exemplary imaging agents include metals (e.g. cobalt, iron, gold), metal salts (e.g. iron oxide, gadolinium salts), near infrared dyes, PET chelating agents, SPECT chelating agents, agents suitable for MRI or Raman spectroscopy, fluorescent dyes and radiopharmaceuticals. Preferred imaging agents are, Nile red, NR668, lipid 780, chlorin e6 and PP9.

The present invention is particularly suitable for active agents featuring functional groups that may initiate premature polymerisation of alkyl cyanoacrylate monomers in the miniemulsion. Such functional groups include M-NH$_3$ (wherein M is a metal), R—NH$_2$, R$_1$R$_2$—NH, R$_1$R$_2$R$_3$N, R$_1$=NR$_2$, R—OH, R—C$_1$, R—Br, R—I, R—SH, RiN=NR$_2$, R—NHOH, structurally associated H$_2$O and enols.

Polymerisation

The process according to the invention provides the preparation of nanoparticles of a poly(alkyl cyanoacrylate) homopolymer or copolymer, wherein said process comprises, in a single step, the anionic polymerisation of an oil-in-water miniemulsion, wherein said miniemulsion comprises
  (i) polymerisable monomers comprising at least one alkyl cyanoacrylate monomer;
  (ii) at least one surfactant, preferably at least one polyalkylene glycol selected from the group consisting of polyethylene glycols (PEG) and polypropylene glycols (PPG), or mixtures thereof;
  (iii) optionally one or more active agents;
  iv) optionally an anionic polymerisation initiator; and
  v) an anionic and radical inhibitor.

The miniemulsion may be prepared by the addition of said at least one surfactant to an oil-in water miniemulsion comprising said at least one alkyl cyanoacrylate monomer, said anionic and radical inhibitor and optionally said one or more active agents. In a preferred embodiment, this addition step and the anionic polymerisation steps are performed consecutively, i.e. the anionic polymerisation step is carried out immediately (e.g., 0-10 minutes, such as 0-5 minutes) after the addition step.

Viewed from an alternative aspect, the processes of the invention comprise the preparation of nanoparticles of a poly(alkyl cyanoacrylate) homopolymer or copolymer, wherein said method comprises adding at least one surfactant, preferably at least one polyalkylene glycol selected from the group consisting of polyethylene glycols (PEG) and polypropylene glycols (PPG), or mixtures thereof, to an oil-in-water miniemulsion, wherein said miniemulsion comprises
  (i) polymerisable monomers comprising at least one alkyl cyanoacrylate monomer;
  (ii) optionally one or more active agents;
  iv) an anionic and radical inhibitor; and polymerising the resulting mixture by anionic polymerisation.

Preferably, the at least one surfactant initiates the anionic polymerisation reaction. However, an additional anionic polymerisation initiator, or pH change, may alternatively be added to the miniemulsion.

The miniemulsion is typically prepared by adding an oil phase containing the monomer(s), the anionic and radical inhibitor, the co-stabiliser and optionally an active agent to an aqueous solution containing the at least one surfactant and subjecting this to high shear forces, e.g. by ultrasonication, to form oil droplets containing the monomer(s) in water. The droplets formed at this stage are a miniemulsion. The presence of the anionic and radical inhibitor prevents a premature polymerisation of the monomer caused by for instance a reactive active agent. Preferably, at least one polyalkylene glycol is present in the aqueous solution acting as the surfactant.

Preferably the polymerisation reaction is carried out at low pH, e.g., pH 1-7. It is preferable if the polymerisation reaction is carried out at temperatures below 50° C., e.g. 4 to 30° C. The resulting blend is a dispersion.

Preferably, the at least one surfactant, preferably at least one polyalkylene glycol, initiates an anionic polymerisation process. Where the polyalkylene glycol initiator has an amino or hydroxide end group, initiation is preferably achieved through nucleophilic attack on the monomer double bond resulting in an anionic or zwitter-ionic polymerisation reaction.

Such processes are well known in the art and hence the mechanisms involved will be well known to the skilled person.

In a particularly preferred embodiment, the anionic polymerisation is combined with radical polymerisation by way of the presence of an additional initiator. This additional initiator will typically be oil soluble and hence commonly be in the oil phase of the miniemulsion, i.e., within the oil droplet. Where these two types of polymerisation are combined, the process of the invention is modified so as to incorporate an increase in temperature, which initiates the radical polymerisation. Typical radical polymerisation initiators include peroxides and azo compounds such as azo-bisdimethyl valeronitril and azoisobutyronitrile.

In one embodiment, the process of the invention may be modified to include crosslinking of the alkyl cyanoacrylate monomers and, if present, co-monomers. This can be facilitated by incorporating a crosslinker, preferably a radically polymerisable crosslinker, into the miniemulsion, preferably within the oil phase. The crosslinker will, in general, be hydrolysed on contact with the aqueous phase, thereby controlling drug release rates and the biodegradability of the nanoparticles. Exemplary crosslinkers include an anhydride, an acrylate or a bis-cyanoacrylate, such as mono- and polyethylene glycol dimethacrylate, dimethacrylate anhydride, 1,6-hexanediol bis-cyanoacrylate or methylene dimethacrylate.

In a further embodiment, the processes of the invention may include a step of raising the temperature (to e.g., 50-70° C.) so as to ensure all residual monomer reacts and/or to initiate crosslinking.

The processes of the present invention may comprise a further step wherein the nanoparticles are isolated. This may be carried out by any known method in the art.

The use of the anionic and radical inhibitors detailed in the present invention provides two main advantages:

Firstly, use of the anionic and radical inhibitors prevents, or limits undesired bulk or mistimed polymerisation allowing the synthesis of nanoparticles with active ingredients that would not otherwise be available to a person skilled in the art. This is observed in two ways, firstly, preventing bulk polymerisation of the ACA monomer when the active ingredient(s) is/are dissolved, enabling nanoparticle synthesis. Further, use of the anionic and radical inhibitors upholds the stability of the oil phase until the miniemulsion is formed, yielding nanoparticles with a low PDI (ideally below 0.200) and size below 300 nm, without excessive precipitation, or microparticle formation.

Secondly, this improved polymerisation by use of the anionic and radical inhibitors removes the need for any of clean-up procedures known in the art, needed to remove by-product bulk polymerisation products or microparticles. Clean-up procedures reduce the yield of nanoparticles and while such methods may be acceptable on a laboratory scale, they would be prohibitively expensive and complex during large scale manufacture. A common clean-up procedure is exemplified in the current disclosure by a centrifugation process commonly used to remove large by-product particles, while leaving behind the nanoparticles suspended in the solution. This method has a key drawback in that it reduces the final concentration (or dry weight) of nanoparticles in solution from the desired 10-20% to <1-5%.

The use of the anionic and radical inhibitors in the process according to the present invention removes or minimizes the need to remove precipitates/microparticles from the final product solution, e.g., by centrifugation.

The advantageous beneficial effects of the anionic and radical inhibitors used in the inventive process are surprising, particularly since these inhibitors outperform known anionic or radical inhibitors.

Nanoparticles

The nanoparticles according to the present invention, and as produced by the processes of the present invention, are different in structure to those produced by emulsion polymerisation. In particular, nanoparticles made by emulsion polymerisation comprise a polymer matrix with any active agent being physically dispersed in that matrix.

Conversely, nanoparticles made by miniemulsion interfacial polymerisation are typically vesicular systems, which contain the active agent in the core of the nanoparticle, surrounded by a polymer shell.

The nanoparticles provided by, and produced in accordance with, the current invention may be formulated as a pharmaceutical composition comprising the nanoparticles together with one or more pharmaceutically acceptable carriers, diluents or excipients. Such carriers, diluents and excipients are well known in the art. The pharmaceutical compositions may also comprise additional active agents. Importantly, the nanoparticles according to the invention are free of toxic inhibitors, such as MSA and BHT, which would render them unsuitable for clinical/pharmaceutical use.

Uses

The nanoparticles and compositions thereof may be used in medicine, in particular in drug delivery and imaging applications. In addition, the nanoparticles may also be highly advantageous in nanoencapsulation of various materials/compounds, such as aroma compounds, fragrances, flavours, dyes, nutraceuticals, herbicides and pesticides. Hence, the present invention relates to nanoparticles according to the present invention for use in medicine and for use in nanoencapsulation of various materials/compounds, such as aroma compounds, fragrances, flavours, dyes, nutraceuticals, herbicides and pesticides.

The nanoparticles and compositions thereof may be used in medicine, in particular in drug delivery and imaging applications. Hence, the present invention relates to nanoparticles according to the present invention for use in medicine. In a further embodiment, the present invention relates to the nanoparticles according to the current invention for use in the treatment or prevention, or the diagnosis of particular disorders and diseases. Examples of disorders or diseases which can be treated or prevented in accordance with the present invention include infections, inflammatory diseases, neurodegenerative diseases, auto-immune diseases, cardiovascular diseases, and cancer, such as lung cancer, breast cancer, prostate cancer, brain cancer, head and neck cancer, ovarian cancer, skin cancer, testicular cancer, pancreatic cancer, colorectal cancer, kidney cancer, cervical cancer, gastrointestinal cancer, bladder cancer and combinations thereof.

The nanoparticles or compositions thereof are preferably administered in a therapeutically effective amount. A "therapeutically effective amount" refers to an amount of the nanoparticles necessary to treat or prevent the particular disease or disorder. Any route of administration may be used to deliver the nanoparticles to the subject. Suitable administration routes include intramuscular injection, transdermal administration, inhalation, topical application, oral administration, rectal or vaginal administration, intratumural administration and parenteral administration (e.g., intravenous, peritoneal, intra-arterial or subcutaneous). The preferable route of administration is injection.

The exact dosage and frequency of administration depends on the particular nanoparticles, active agent and optional targeting agents used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the nanoparticles according to the instant invention.

Experimental Part

In the following, detailed examples of preparation of nanoparticles using the process according to the present invention are described.

The results of the experimental examples are summarized in Table 2.

The nanoparticles are characterized by their size, polydispersity index and zeta potential, as well as whether centrifugation of the final solution of nanoparticles was required to isolate the nanoparticles due to formation of unwanted precipitates/microparticles.

The polydispersity index is defined in context of measurement of particle size by dynamic light scattering as given by Malvern Panalytics, and is the number calculated from a 2-parameter fit to the correlation data (cumulants analysis). Calculations for this are defined in ISO standard documents ISO 13321:1996 E, and ISO 22412:2008. It is generally accepted that >0.7 give a very broad distribution of size and is not suitable for DLS techniques, and 0.05 is highly monodisperse. For purposes of our particles, preferred 0.05-0.300, most preferred 0.100 to 0.200.

The zeta potential is the measure of the electric potential in the interfacial double layer of the suspended particles, and is often given as measure of the stability of a colloidal dispersion. Nanoparticles for biomedical applications, with high zeta potential tend to adsorb protein, and thus will be targeted by the immune system, reducing circulation time and efficacy. Particles with low zeta potential and steric stabilisation containing hydrogen bond donators (e.g., PEG containing surfactant) have a longer circulation time. As such, a zeta potential of 20 to −20 is preferred, 10 to −10 is more preferred and 5 to −5 is most preferred.

Dry weight w/w % is the non-volatile material content of the batch, after removal by centrifugation of any solids that are not of nanoparticle size. The dry weight is commonly in the range of 1-25 w/w %, preferably 5-20 w/w % and most preferably 10-20 w/w %. The w/w refers to weight of nanoparticles vs. weight of the volatiles in mixture (usually water and HCl).

As supported by the experimental data, the anionic and radical inhibitors comprising an aromatic aldehyde group, i.e., vanillin, 4-hydroxy-3,5-dimethylbenzaldehyde, 4-hydroxy-3,5-dimethoxybenzaldehyde, salicylaldehyde and benzaldehyde, are superior to vitamin E, vitamin K3 and vitamin K1. Notably, the solution of nanoparticles obtained by use of the anionic and radical inhibitors comprising an aromatic aldehyde group did not have to be centrifuged since no or minimal amount of precipitate/microparticles were formed.

It is noted that the anionic inhibitor activity of vitamin E, vitamin K3 and vitamin K1 is much weaker than for the benzaldehyde-type inhibitors. The weak anionic inhibitor activity is believed to at least partly be the cause of the increased formation of precipitates/microparticles observed for these inhibitors.

EXAMPLES

In the following, a number of experimental examples are presented. These include embodiments of the invention using anionic and radical inhibitors (i.e., a single compound able to inhibit both anionic and radical polymerisation), as well as comparative examples. The comparative examples include examples wherein known anionic or radical inhibitors are used.

A selection of the experimental examples is presented in more detail below. The remaining examples were performed by experimental procedures similar to the ones disclosed, by simply replacing the relevant reactants and solvents by the ones listed in table 2.

Figure 1E:
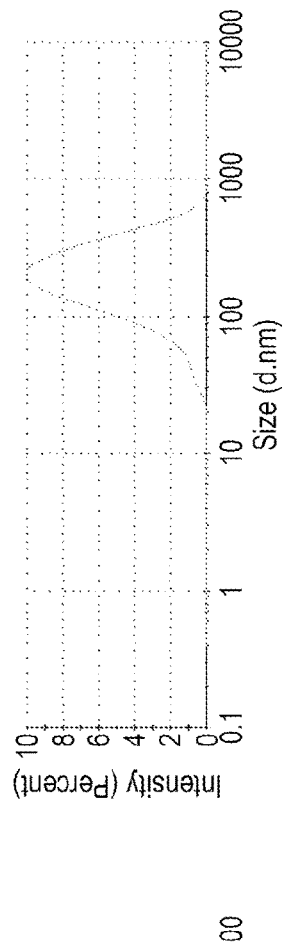
Figure 1G:
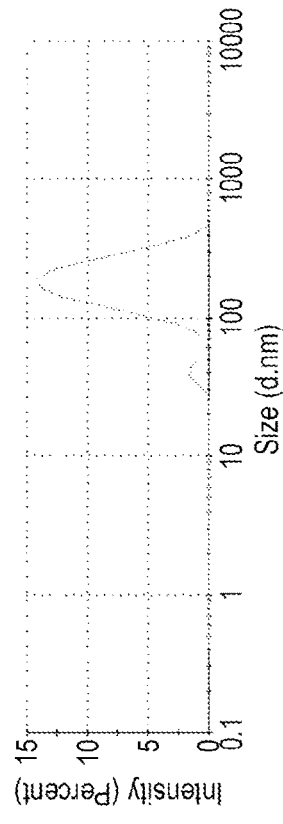
Figure 1F:
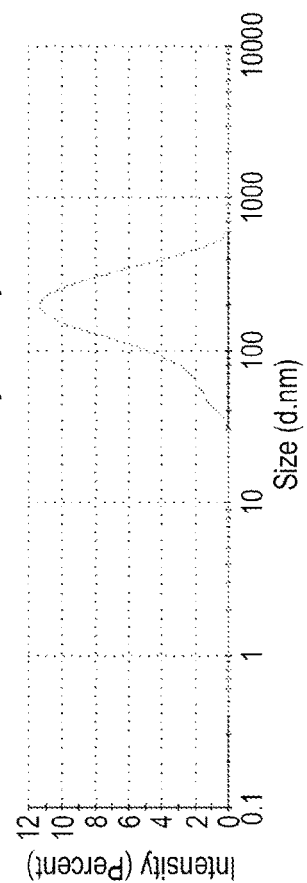
Figure 1H:
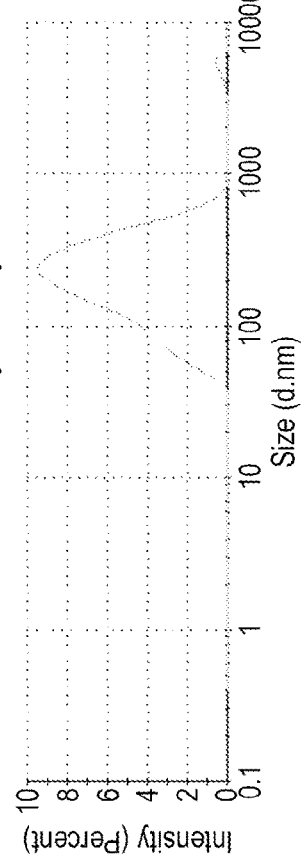
Figure 1I:
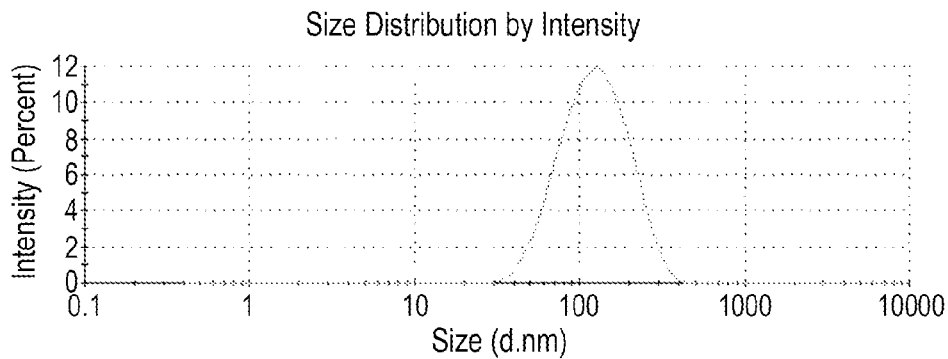
Figure 1J:
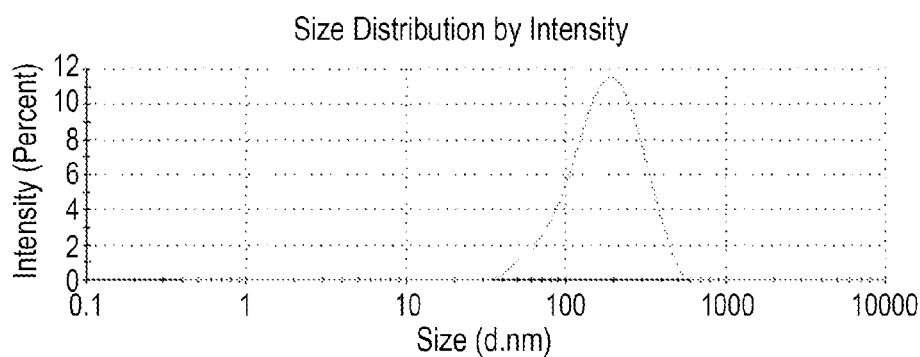
Figure 1K:
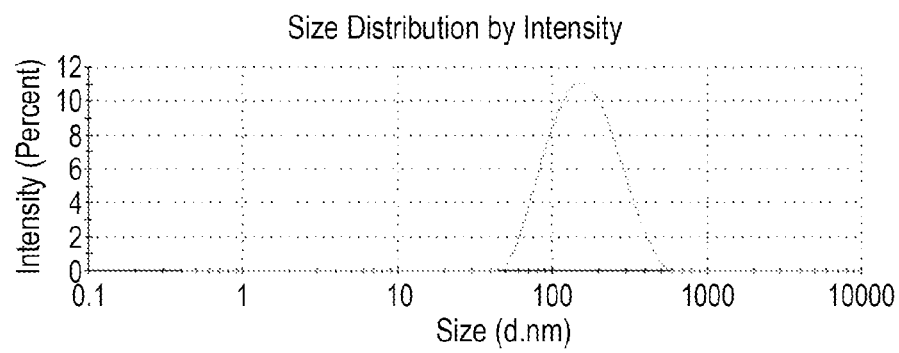
Figure 1L:
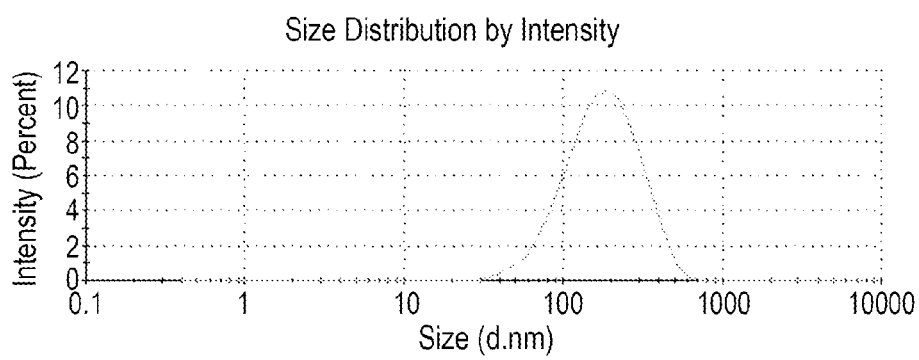
Figure 1M:
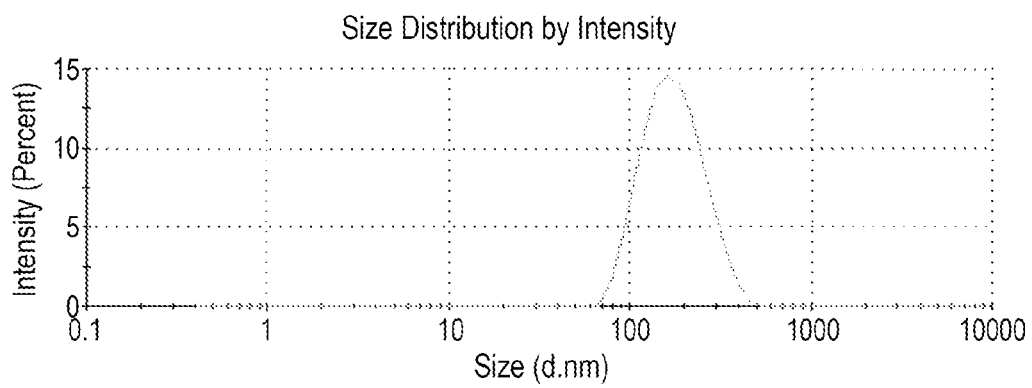

Size by distribution plots from selected examples, before and after centrifugation, are shown in table 3 and FIGS. 1A-1M. The advantageous effect of using aromatic aldehyde type anionic and radical inhibitors is apparent when compared to experimental examples using anionic and radical inhibitors not containing an aromatic aldehyde group (i.e. vitamins E, K1 and K3).

The experimental examples include the following anionic and radical inhibitors (i.e. double inhibitors):

Vanillin:

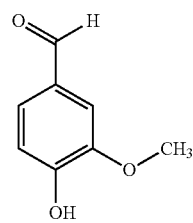

Vitamin K1:

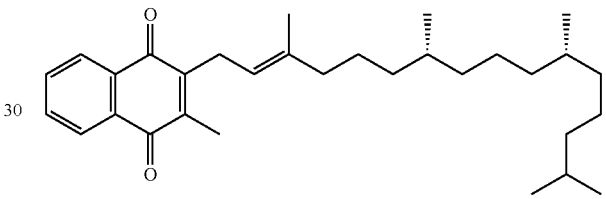

Vitamin K3:

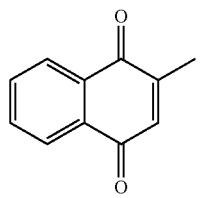

Vitamin E:

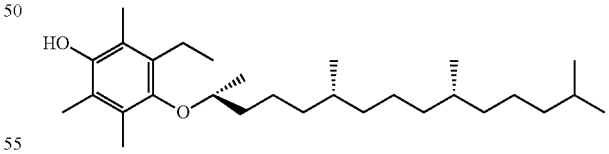

Salicylaldehyde:

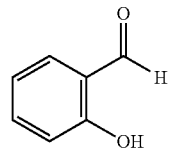

Benzaldehyde:

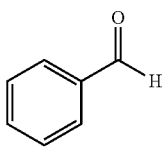

4-Hydroxy-3,5-dimethylbenzaldehyde (DMHB):

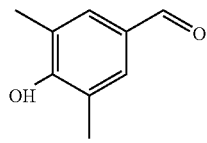

4-Hydroxy-3,5-dimethoxybenzaldehyde (HDMB):

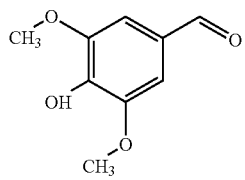

The experimental examples include the following prior art anionic or radical inhibitors:

Methanesulfonic acid (MSA)—Anionic Inhibitor:

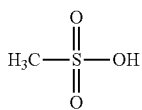

Butylated hydroxytoluene (BHT)—Radical Inhibitor:

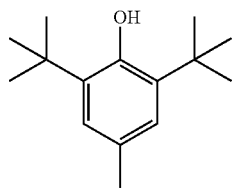 [SMILES: Cc1cc(C(C)(C)C)c(O)c(C(C)(C)C)c1]

Butylated hydroxyanisole (BHA)—Radical Inhibitor:

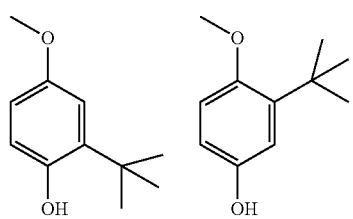

All examples were performed using the miniemulsion method.

Example 1 (Comparative): Particle Synthesis with a 0.18% DiR Dye, with a Radical Inhibitor (BHT)

Solution 1 (aqueous phase): 120 mg of Kolliphor® HS 15 (Sigma Aldrich), 0.120 g Brij® L23 (Sigma Aldrich) and 12.0 g of 0.1 M hydrochloric acid solution (Merck) water were mixed in a glass vial until the solids were completely dissolved.

Solution 2 (monomer phase): 0.80 g of n-butyl cyanoacrylate (monomer, Henkel Loctite, Ireland), 0.010 g of butylated hydroxy toluene (BHT, Fluka) and 0.060 g solution of the dye DiR (Marker Gene Technology) dissolved in Miglyol® 812 (Caeser and Loretz GmBH, such that 1.6 mg of DiR was added to the mixture) were thoroughly mixed in a glass vial. Solution 1 and 2 were mixed for 30 seconds in a 20 ml glass vial placed on ice using a magnetic stirrer. The oil-in water emulsion was immediately sonicated for 3 minutes (6×30 sec intervals) on ice (Branson Sonifier® digital 450 CE, 25% amplitude). After sonication, the formed miniemulsion was polymerized over night at room temperature on rotation (15 rpm), then the pH was adjusted to pH 5.

The particle size and their zeta potential was determined using Malvern Nano Series zetasizer. Optionally, centrifugation was used to isolate the nanoparticles from large by-product particles, and the nanoparticle solution re-analyzed (see Table 2).

The nanoparticles that were obtained had 615 nm (z-average diameter) with a polydispersity index of 0.63. The result was sufficiently poor that further analysis was not obtained.

Example 5: Particle Synthesis with a 0.10% DiR Dye, with a Double Inhibitor (Vanillin)

Solution 1 (aqueous phase): 125 mg of Kolliphor® HS 15 (Sigma Aldrich), 0.125 g Brij® L23 (Sigma Aldrich) and 11.5 g of 0.1 M hydrochloric acid solution (Merck) water were mixed in a glass vial until the solids were completely dissolved.

Solution 2 (monomer phase): 2.25 g of n-butyl cyanoacrylate (monomer, Henkel Loctite, Ireland), 0.240 g of vanillin (Sigma Aldrich) and 0.100 g solution of the dye DiR (Marker Gene Technology) dissolved in Miglyol® 812 (Caeser and Loretz GmBH, such that 2.6 mg of DiR was added to the mixture) were thoroughly mixed in a glass vial. Solution 1 and 2 were mixed for 30 seconds in a 20 ml glass vial placed on ice using a magnetic stirrer. The oil-in water emulsion was immediately sonicated for 3 minutes (6×30 sec intervals) on ice (Branson Sonifier® digital 450 CE, 25% amplitude). After sonication, the formed miniemulsion was polymerized over night at room temperature on rotation (15 rpm), then the pH was adjusted to pH 5.

The particle size and their zeta potential were determined using Malvern Nano Series zetasizer. Optionally, centrifugation was used to isolate the nanoparticles from large by-product particles, and the nanoparticle solution re-analyzed (see Table 2).

The nanoparticles that were obtained had 158 nm (z-average diameter) with a polydispersity index of 0.11, zeta potential of −3.4 mV and nanoparticle concentration of (w/w).

Example 7 (Comparative): Particle Synthesis with a 0.6% NR668 Dye, without any Inhibitor (Negative Control)

Solution 1 (aqueous phase): 120 mg of Kolliphor® HS 15 (Sigma Aldrich), 0.120 g Brij® L23 (Sigma Aldrich) and 12.0 g of 0.1 M hydrochloric acid solution (Merck) water were mixed in a glass vial until the solids were completely dissolved.

Solution 2 (monomer phase): 0.80 g of n-butyl cyanoacrylate (monomer, Henkel Loctite, Ireland), and 0.048 g solution of the dye NR668 (Modified Nile red, SINTEF) dissolved in Miglyol® 812 (Caeser and Loretz GmBH, such that 5.1 mg of NR668 was added to the mixture) were thoroughly mixed in a glass vial.

Solution 1 and 2 were mixed for 30 seconds in a 20 ml glass vial placed on ice using a magnetic stirrer. The oil-in water emulsion was immediately sonicated for 3 minutes (6×30 sec intervals) on ice (Branson Sonifier® digital 450 CE, 25% amplitude). After sonication, the formed mini-emulsion was polymerized over night at room temperature on rotation (15 rpm), then the pH was adjusted to pH 5.

The particle size and their zeta potential were determined using Malvern Nano Series zetasizer. Optionally, centrifugation was used to isolate the nanoparticles from large by-product particles, and the nanoparticle solution re-analyzed (see Table 2).

The above-mentioned method resulted in partial polymerization before the solutions could be blended. What liquid monomer solution remained was used, and the nanoparticles that were obtained had 148 nm (z-average diameter) with a polydispersity index of 0.27, zeta potential of −3.66 mV and nanoparticle concentration of 4.1% (w/w).

Example 10 (Comparative): Particle Synthesis with a 0.6% NR668 Dye, with a Radical Inhibitor (BHT)

Solution 1 (aqueous phase): 120 mg of Kolliphor® HS 15 (Sigma Aldrich), 0.120 g Brij® L23 (Sigma Aldrich) and 12.0 g of 0.1 M hydrochloric acid solution (Merck) water were mixed in a glass vial until the solids were completely dissolved.

Solution 2 (monomer phase): 0.80 g of n-butyl cyanoacrylate (monomer, Henkel Loctite, Ireland), 0.043 g of butylated hydroxytoluene (BHT, Fluka) and 0.050 g solution of the dye NR668 (Modified Nile red, SINTEF) dissolved in Miglyol® 812 (Caeser and Loretz GmBH, such that 5.3 mg of NR668 was added to the mixture) were thoroughly mixed in a glass vial.

Solution 1 and 2 were mixed for 30 seconds in a 20 ml glass vial placed on ice using a magnetic stirrer. The oil-in water emulsion was immediately sonicated for 3 minutes (6×30 sec intervals) on ice (Branson Sonifier® digital 450 CE, 25% amplitude). After sonication, the formed mini-emulsion was polymerized over night at room temperature on rotation (15 rpm), then the pH was adjusted to pH 5.

The particle size and their zeta potential were determined using Malvern Nano Series zetasizer. Optionally, centrifugation was used to isolate the nanoparticles from large by-product particles, and the nanoparticle solution re-analyzed (see Table 2).

The nanoparticles that were obtained had 164.2 nm (z-average diameter) with a polydispersity index of 0.24, zeta-potential of −3.90 mV.

Example 12 (Comparative): Particle Synthesis with a 0.2% NR668 Dye, with an Anionic Inhibitor (MSA)

Solution 1 (aqueous phase): 120 mg of Kolliphor® HS 15 (Sigma Aldrich), 0.120 g Brij® L23 (Sigma Aldrich) and 12.0 g of 0.1 M hydrochloric acid solution (Merck) water were mixed in a glass vial until the solids were completely dissolved.

Solution 2 (monomer phase): 0.80 g of n-butyl cyanoacrylate (monomer, Henkel Loctite, Ireland), 0.002 g of methane sulfonic acid (Sigma Aldrich) and 0.020 g solution of the dye NR668 (Modified Nile red, SINTEF) dissolved in Miglyol® 812 (Caeser and Loretz GmBH, such that 2.1 mg of NR668 was added to the mixture) were thoroughly mixed in a glass vial.

Solution 1 and 2 were mixed for 30 seconds in a 20 ml glass vial placed on ice using a magnetic stirrer. The oil-in water emulsion was immediately sonicated for 3 minutes (6×30 sec intervals) on ice (Branson Sonifier® digital 450 CE, 25% amplitude). After sonication, the formed mini-emulsion was polymerized over night at room temperature on rotation (15 rpm), then the pH was adjusted to pH 5.

The particle size and their zeta potential were determined using Malvern Nano Series zetasizer. Optionally, centrifugation was used to isolate the nanoparticles from large by-product particles, and the nanoparticle solution re-analyzed (see Table 2).

The nanoparticles that were obtained had 201 nm (z-average diameter) with a polydispersity index of 0.33, zeta-potential of −4.79 mV and nanoparticle concentration of 6.0% (w/w).

Example 13 (Comparative): Particle Synthesis with a 0.2% NR668 Dye, with a Radical Inhibitor (BHA)

The particles of example 13 were obtained by using the same experimental procedure as disclosed for example 16, using BHA instead of vanillin.

Example 16: Particle Synthesis with a 0.2% NR668 Dye, Using a Double Inhibitor (Vanillin)

Solution 1 (aqueous phase): 120 mg of Kolliphor® HS 15 (Sigma Aldrich), 0.120 g Brij® L23 (Sigma Aldrich) and 12.0 g of 0.1 M hydrochloric acid solution (Merck) water were mixed in a glass vial until the solids were completely dissolved.

Solution 2 (monomer phase): 0.80 g of n-butyl cyanoacrylate (BCA, monomer, Henkel Loctite, Ireland), 0.040 g of vanillin (Sigma Aldrich) and 0.020 g solution of the dye NR668 (Modified Nile red, SINTEF) dissolved in Miglyol® 812 (Caeser and Loretz GmBH, such that 2.1 mg of NR668 was added to the mixture) were thoroughly mixed in a glass vial.

Solution 1 and 2 were mixed for 30 seconds in a 20 ml glass vial placed on ice using a magnetic stirrer. The oil-in water emulsion was immediately sonicated for 3 minutes (6×30 sec intervals) on ice (Branson Sonifier® digital 450 CE, 25% amplitude). After sonication, the formed mini-emulsion was polymerized over night at room temperature on rotation (15 rpm), then the pH was adjusted to pH 5.

The particle size and their zeta potential were determined using Malvern Nano Series zetasizer. Optionally, centrifugation was used to isolate the nanoparticles from large by-product particles, and the nanoparticle solution re-analyzed (see Table 2).

The nanoparticles that were obtained had 112 nm (z-average diameter) with a polydispersity index of 0.23, zeta-potential of −3.45 mV and nanoparticle concentration of 6.6% (w/w).

Example 20: Particle Synthesis with a 0.6% NR668 Dye, with a Double Inhibitor (HDMB) Using the Miniemulsion Method Solution 1 (aqueous phase): 120 mg of Kolliphor® HS 15 (Sigma Aldrich), 0.120 g Brij® L23 (Sigma Aldrich) and 12.0 g of 0.1 M hydrochloric acid solution (Merck) water were mixed in a glass vial until the solids were completely dissolved.

Solution 2 (monomer phase): 0.80 g of n-butyl cyanoacrylate (monomer, Henkel Loctite, Ireland), 0.043 g of 4-hydroxy-3,5-dimethoxy-benzaldehyde (HMDB, Sigma Aldrich) and 0.050 g solution of the dye NR668 (Modified Nile red, SINTEF) dissolved in Miglyol® 812 (Caeser and Loretz GmBH, such that 5.3 mg of NR668 was added to the mixture) were thoroughly mixed in a glass vial.

Solution 1 and 2 were mixed for 30 seconds in a 20 ml glass vial placed on ice using a magnetic stirrer. The oil-in water emulsion was immediately sonicated for 3 minutes (6×30 sec intervals) on ice (Branson Sonifier® digital 450 CE, 25% amplitude). After sonication, the formed miniemulsion was polymerized over night at room temperature on rotation (15 rpm), then the pH was adjusted to pH 5.

The particle size and their zeta potential were determined using Malvern Nano Series zetasizer. Optionally, centrifugation was used to isolate the nanoparticles from large by-product particles, and the nanoparticle solution re-analyzed (see Table 2).

The nanoparticles that were obtained had 154 nm (z-average diameter) with a polydispersity index of 0.20, zeta-potential of −3.90 mV and nanoparticle concentration of 6.0% (w/w).

Comparative Examples 8, 9, 11, 14, and Examples 15, 17, 18 and 19

The particles of examples 8, 9, 11, 14, 15, 17, 18 and 19 were obtained by using the same experimental procedure as disclosed for example 20 and changing the type of inhibitor.

Example 39: Stealth Particles with Approximately 0.15% Targeting Moieties (PEG Folate Targeting)

Solution 1 (PEG/targeting ligand): 15 mg of DSPE-PEG (2000)-folate and 5.0 g of distilled water were mixed in a glass vial, pH adjusted to pH 6 with 5M HCl and degassed using N2 for 15 minutes.

Solution 2 (monomer phase): 0.45 g of n-butyl cyanoacrylate (monomer, Henkel Loctie, Ireland), and 0.015 g solution of the dye NR668 (Modified Nile red, SINTEF) dissolved in Miglyol® 812 (Caeser and Loretz GmBH, such that 2.0 mg of NR668 was added to the mixture) were thoroughly mixed in a glass vial.

Solution 3 (stabilizer): 30 mg of Kolliphor® HS 15 (Sigma Aldrich), 30 mg Brij® L23 (Sigma Aldrich) and 5.0 g of 0.1 M hydrochloric acid solution (Merck) water were mixed in a glass vial until the solids were completely dissolved.

Solution 1, 2 and 3 were mixed for 30 seconds in a 5 ml glass vial placed on ice using a magnetic stirrer. The oil-in water emulsion was immediately sonicated for 3 minutes (6×30 sec intervals) on ice (Branson Sonifier® digital 450 CE, 25% amplitude) and polymerized over night at room temperature on rotation (15 rpm). The pH was adjusted to pH 5 and the solution was dialyzed (Spectra/Por dialysis membrane MWCO 12-14000) extensively against distilled water at room temperature to remove surfactant and unreacted PEG. The particle size and their zeta potential were determined using Malvern Nano Series zetasizer. Optionally, centrifugation was used to isolate the nanoparticles from large by-product particles, and the nanoparticle solution re-analyzed (see Table 2). The above-mentioned method resulted in PEGylated, targeted nanoparticles of 170 nm (z-average diameter) with a polydispersity index of 0.17, zeta potential of −9 mV and nanoparticle concentration of 1.80% (w/w).

Example 41: Particle Synthesis with a 1.8% PP9 Dye, with a Double Inhibitor (Vanillin)

Solution 1 (aqueous phase): 60 mg of Kolliphor® HS 15 (Sigma Aldrich), 60 mg Brij® L23 (Sigma Aldrich) and 6.0 g of 0.1 M hydrochloric acid solution (Merck) water were mixed in a glass vial until the solids were completely dissolved.

Solution 2 (monomer phase): 1.01 g of n-octyl cyanoacrylate (monomer, Henkel Loctite, Ireland), 0.050 g of vanillin (Sigma Aldrich), 0.020 g solution of the dye PP9 (Protoporphyrin IX, Sigma Aldrich) and 0.019 g Miglyol® 812 (Caeser and Loretz GmBH), were thoroughly mixed in a glass vial.

Solution 1 and 2 were mixed for 30 seconds in a 20 ml glass vial placed on ice using a magnetic stirrer. The oil-in water emulsion was immediately sonicated for 3 minutes (6×30 sec intervals) on ice (Branson Sonifier® digital 450 CE, 25% amplitude). After sonication, the formed miniemulsion was polymerized over night at room temperature on rotation (15 rpm), the pH was adjusted to pH 5 and the sample dialyzed (3×1 L, 1 mM HCl). The particle size and their zeta potential were determined using Malvern Nano Series zetasizer. Optionally, centrifugation was used to isolate the nanoparticles from large by-product particles, and the nanoparticle solution re-analyzed (see Table 2). The nanoparticles that were obtained had 174 nm (z-average diameter) with a polydispersity index of 0.26, zeta potential of −2.6 mV and nanoparticle concentration of 6.9% (w/w).

Example 42: Particle Synthesis with a 0.22% NR668 Dye and API (18.6% Cabazitaxel), with a Double Inhibitor (Vanillin)

Solution 1 (aqueous phase): 50 mg of Kolliphor HS 15 (Sigma Aldrich), 0.100 g Pluronic® F68 and 6.0 g of 0.1 M hydrochloric acid solution (Merck) water were mixed in a glass vial until the solids were completely dissolved.

Solution 2 (monomer phase): 0.5 g of ethylbutylcyanoacrylate (monomer, SINTEF), 0.030 g of vanillin (Sigma Aldrich), 0,125 g cabazitaxel (Biochempartner, China) and 0.015 g solution of the dye NR668 (Modified Nile red, SINTEF) dissolved in Miglyol 812 (Caeser and Loretz GmBH, such that 2.1 mg of NR668 was added to the mixture) were thoroughly mixed in a glass vial.

Solution 1 and 2 were mixed for 30 seconds in a 20 ml glass vial placed on ice using a magnetic stirrer. The oil-in water emulsion was immediately sonicated for 3 minutes (6×30 sec intervals) on ice (Branson Sonifier® digital 450 CE, 25% amplitude). After sonication, the formed miniemulsion was polymerized over night at room temperature on rotation (15 rpm), then the pH was adjusted to pH 5 and dialyzed extensively against distilled water.

The particle size and their zeta potential were determined using Malvern Nano Series zetasizer. Optionally, centrifugation was used to isolate the nanoparticles from large by-product particles, and the nanoparticle solution re-analyzed (see Table 2).

The nanoparticles that were obtained had 175 nm (z-average diameter) with a polydispersity index of 0.22, zeta-potential of −3.10 mV and nanoparticle concentration of 1.19% (w/w).

Example 43: Particle Synthesis with a 0.24% Lipid 780 and API (23% Cabazitaxel), with a Double Inhibitor (Vanillin)

Solution 1 (aqueous phase): 30 mg of Kolliphor HS 15 (Sigma Aldrich), 0.130 g Pluronic® F68 and 6 g of 0.1 M hydrochloric acid solution (Merck) water were mixed in a glass vial until the solids were completely dissolved.

Solution 2 (monomer phase): 0.450 g of ethyl butyl cyanoacrylate (monomer, Henkel Loctite, Ireland), 0.030 g of vanillin (Sigma Aldrich) and, and 0.150 g cabazitaxel (Biochempartner, China), 0.024 g solution of the dye Lipid 780 (CEA chemicals) dissolved in Miglyol® 812 (Caeser and Loretz GmBH, such that 14 mg of Lipid 780 was added to the mixture) were thoroughly mixed in a glass vial.

Solution 1 and 2 were mixed for 30 seconds in a 20 ml glass vial placed on ice using a magnetic stirrer. The oil-in water emulsion was immediately sonicated for 3 minutes (6×30 sec intervals) on ice (Branson Sonifier® digital 450 CE, 25% amplitude). After sonication, the formed miniemulsion was polymerized over night at room temperature on rotation (15 rpm), then the pH was adjusted to pH 5.

The particle size and their zeta potential were determined using Malvern Nano Series zetasizer. Optionally, centrifugation was used to isolate the nanoparticles from large by-product particles, and the nanoparticle solution re-analyzed (see Table 2).

The nanoparticles that were obtained had 118 nm (z-average diameter) with a polydispersity index of 0.18, zeta-potential of −2.00 mV and nanoparticle concentration of 1.05% (w/w).

Example 44: Particle Synthesis with an API (10% Cabazitaxel) with a Double Inhibitor (Vanillin)

Solution 1 (aqueous phase): 150 mg of Kolliphor HS® 15 (Sigma Aldrich), 0.150 g Brij® L23 (Sigma Aldrich) and 18.0 g of 0.1 M hydrochloric acid solution (Merck) water were mixed in a glass vial until the solids were completely dissolved.

Solution 2 (monomer phase): 2.25 g of ethylbutylcyanoacrylate (monomer, Cuantum medical, Spain), 0.060 g of vanillin (Sigma Aldrich) and 0.270 g cabazitaxel (Biochempartner, China) were thoroughly mixed in a glass vial.

Solution 1 and 2 were mixed for 30 seconds in a 20 ml glass vial placed on ice using a magnetic stirrer. The oil-in water emulsion was immediately sonicated for 3 minutes (6×30 sec intervals) on ice (Branson Sonifier digital 450 CE, 25% amplitude). After sonication, the formed miniemulsion was polymerized over night at room temperature on rotation (15 rpm), then the pH was adjusted to pH 5 and the solution dialyzed against 1 mM hydrochloric acid (aqueous, Merck).

The particle size and their zeta potential were determined using Malvern Nano Series zetasizer. Optionally, centrifugation was used to isolate the nanoparticles from large by-product particles, and the nanoparticle solution re-analyzed (see Table 2).

The nanoparticles that were obtained had 163 nm (z-average diameter) with a polydispersity index of 0.14, zeta potential of −2.80 mV and nanoparticle concentration of (w/w).

TABLE 2

| Pt. No. | ACA | Inhibitor | Amount [% of the oil phase] | PEG/initiator And Stabiliser | Active ingredients | Centrifuged? | z-average pH 7 (nm) | PDI | Zeta potential pH 7 (mV) | Dry weight w/w % | Result |
|---|---|---|---|---|---|---|---|---|---|---|---|
| 1 | BCA | BHT | 1.15 | Kolliphor® HS15 + Brij® L23 | 0.18% DiR i Miglyol® 812 | No | 615 | 0.64 | | | Failed |
| 2 | BCA | BHA | 1.15 | Kolliphor® HS15 + Brij® L23 | 0.18% DiR i Miglyol® 812 | No | 151 | 0.44 | | | Failed |
| 3 | BCA | BHA | 4.8 | Kolliphor® HS15 + Brij® L23 | 0.18% DiR i Miglyol® 812 | No | 1029 | 0.038 | | | Failed |
| 4 | BCA | Vanillin/BHT | 8.4/0.2 | Kolliphor® HS15 + Pluronic® F68 | 0.14% DiR i Miglyol® 10.1% Cabazitaxel | Yes | 398 | 0.28 | | 0.8 | Poor |
| 5 | BCA | Vanillin | 10 | Kolliphor® HS15 + Brij® L23 | 0.1% DiR i Miglyol® | Not required | 158 | 0.11 | −3.4 | 15.1 | Good |
| 6 | BCA | Vanillin | 9 | Kolliphor® HS15 + Pluronic® F68 | 0.1% DiR i Miglyol® 13% Cabazitaxel | Yes | 209 | 0.10 | | 0.6 | Poor |
| 7 | BCA | — | — | Kolliphor® HS15 + Brij® L23 | 0.6% NR668 i Miglyol 812 | Yes | 148 | 0.27 | −3.66 | 4.1 | Okay |
| 8 | BCA | Vitamin K1 | 4.8 | Kolliphor® HS15 + Brij® L23 | 0.60% NR-668 | Yes | 158.8 | 0.23 | −3.38 | 4.3 | Okay |
| 9 | BCA | Vitamin K3 | 4.98 | Kolliphor® HS15 + Brij® L23 | 0.60% NR-668 | Yes | 178.2 | 0.32 | −4.04 | — | Okay |
| 10 | BCA | BHT | 4.8 | Kolliphor® HS15 + Brij® L23 | 0.60% NR-668 | Yes | 164.2 | 0.24 | −2.35 | — | Okay |

TABLE 2-continued

| Pt. No. | ACA | Inhibitor | Amount [% of the oil phase] | PEG/initiator And Stabiliser | Active ingredients | Centrifuged? | z-average pH 7 (nm) | PDI | Zeta potential pH 7 (mV) | Dry weight w/w % | Result |
|---|---|---|---|---|---|---|---|---|---|---|---|
| 11 | BCA | Vitamin E | 4.8 | Kolliphor® HS15 + Brij® L23 | 0.60% NR-668 | Yes | 167.1 | 0.27 | −2.47 | — | Okay |
| 12 | BCA | MSA | 0.2 | Kolliphor® HS15 + Brij® L23 | 0.2% NR668 i Miglyol® 812 | Not required | 201 | 0.33 | −4.79 | 6.0 | Okay |
| 13 | BCA | BHA | 4.7 | Kolliphor® HS15 + Brij® L23 | 0.2% NR668 i Miglyol® 812 | Not required | 116 | 0.14 | −2.73 | 6.5 | Good |
| 14 | BCA | Vitamin E | 4.8 | Kolliphor® HS15 + Brij® L23 | 0.6% NR668 i Miglyol® 812 | Yes | 156 | 0.21 | −2.11 | 5.1 | Okay |
| 15 | BCA | Salicylaldehyd | 4.8 | Kolliphor® HS15 + Brij® L23 | 0.6% NR668 i Miglyol® 812 | Yes | 158 | 0.42 | −2.81 | 3.8 | Poor |
| 16 | BCA | Vanillin | 4.7 | Kolliphor® HS15 + Brij® L23 | 0.2% NR668 i Miglyol® 812 | Not required | 112 | 0.17 | −3.45 | 6.6 | Good |
| 17 | BCA | Vanillin | 4.8 | Kolliphor® HS15 + Brij® L23 | 0.6% NR668 i Miglyol® 812 | Not required | 122 | 0.174 | −5.59 | 7.0 | Good |
| 18 | BCA | Benzaldehyd | 4.8 | Kolliphor® HS15 + Brij® L23 | 0.6% NR668 i Miglyol® 812 | Not required | 156 | 0.19 | −3.01 | 6.2 | Good |
| 19 | BCA | DMHB | 4.8 | Kolliphor® HS15 + Brij® L23 | 0.60% NR-668 | Not required | 142.5 | 0.18 | −3 | 6.9 | Good |
| 20 | BCA | HDMB | 4.8 | Kolliphor® HS15 + Brij® L23 | 0.60% NR-668 | Not required | 154 | 0.2 | −3.9 | 6 | Good |
| 21 | BCA | Vanillin | 4.6 | Kolliphor® HS15 + Brij® L23 | 14.4% Cloxacillin acid form and 2% Miglyol® 812 | Not required | 143 | 0.32 | −15.5 | 8.4 | Okay |
| 22 | BCA | Vanillin | 4.6 | Kolliphor® HS15 + Brij® L23 | 14.4% oxacillin acid form and 2% Miglyol® 812 | Not required | 143 | 0.26 | −17.4 | 8.7 | Okay |
| 23 | BCA | vanillin | 4.6 | Kolliphor® HS15 + Pluronic® F68 | 25% cabazitaxel and 3% Miglyol® 812 | Not required | 137 | 0.16 | −2 | 4.4 | Good |
| 24 | BCA | vanillin | 2.3 | Kolliphor® HS15 + Brij® L23 | 10.2% cabazitaxel, NR668 and 2.3% Miglyol® 812 | Not required | 188 | 0.14 | −4.3 | 10.7 | Good |
| 25 | EBCA | Vanillin | 2 | Kolliphor® HS15 + Brij® L23 | 5% ispinesin and Miglyol® 812 | Not required | 78 | 0.23 | | | Good |
| 26 | EBCA | vanillin | 2.3 | Kolliphor® HS15 + Brij® L23 | 10.2% cabazitaxel, NR668 and 2.3% Miglyol® 812 | Not required | 165 | 0.17 | −2 | 8.7 | Good |
| 27 | EBCA | vanillin | 4.6 | Kolliphor® HS15 + Pluronic® F68 | 25% cabazitaxel and 3% Miglyol® 812 | Yes | 126 | 0.16 | −2 | 0.3 | Poor |
| 28 | EBCA | Vanillin | 4.6 | Kolliphor® HS15 + Brij® L23 | 14.4% Cloxacillin acid form and 2% Miglyol® 812 | Yes | 117 | 0.33 | −23.7 | 7.3 | Poor |
| 29 | EBCA | Vanillin | 10 | Kolliphor® HS15 + Brij® L23 | 5% daptomycin and 2% miglyol 812 | Yes | 332 | 0.45 | −41.6 | 3.1 | Poor |

TABLE 2-continued

| Pt. No. | ACA | Inhibitor | Amount [% of the oil phase] | PEG/initiator And Stabiliser | Active ingredients | Centrifuged? | z-average pH 7 (nm) | PDI | Zeta potential pH 7 (mV) | Dry weight w/w % | Result |
|---|---|---|---|---|---|---|---|---|---|---|---|
| 30 | EBCA | Vanillin | 10 | Kolliphor® HS15 + Brij® L23 | 15% cloxacillin and 5% daptomycin and 2% Miglyol® 812 | Not required | 142 | 0.18 | −50.6 | 2.9 | Good |
| 31 | EBCA | Vanillin | 5 | Kolliphor® HS15 + Brij® L23 | 6% oxacillin acid form and 2% Miglyol® 812 | Not required | 197 | 0.183 | −31.7 | 3.3 | Good |
| 32 | EBCA | vanillin | 10 | Kolliphor® HS15 + Pluronic® F68 | 0.26% NR668 and 2.6% Miglyol® 812 | Yes | 226 | 0.26 | −2.8 | 2.95 | Poor |
| 33 | EBCA | Vanillin | 10 | Kolliphor® HS15 + Brij® L23 | 0.1% DIR and 3.9% Miglyol® 812 | Not required | 193 | 0.12 | −0.7 | 2.1 | Good |
| 34 | OCA | Vanillin | 5 | Kolliphor® HS15 + Brij® 35 | 3% PP9 and Miglyol® 812 | Not required | 203 | 0.26 | −3.7 | 7.3 | Okay |
| 35 | OCA | Vanillin | 5 | Kolliphor® HS15 + Brij® 35 | 3% Chlorine 6 and Miglyol® 812 | Yes | 145 | 0.22 | −7.2 | 7.0 | Poor |
| 36 | OCA | vanillin | 2.3 | Kolliphor® HS15 + Brij® L23 | 10.2% cabazitaxel, 0.22% NR668 and 2.3% Miglyol® 812 | Not required | 150 | 0.18 | −3.8 | 8.8 | Good |
| 37 | OCA | Vanillin | 5 | Kolliphor® HS15 + Brij® 35 | 2% NR668 and Miglyol® 812 | Yes | 199 | 0.24 | −2.0 | 6.1 | Good |
| 38 | OCA | vanillin | 9 | Kolliphor® HS15 + Pluronic® F68 | 13% cabazitaxel, 0.1% DIR and Miglyol® 812 | Yes | 181 | 0.18 | −0.5 | 1.9 | Poor |
| 39 | BCA | Vanillin | 10 | Kolliphor® HS15 + Brij® 35 | 7.7% DSPE-PEG(2000)-folat. 0.3% NR668 and Miglyol® 812 | Not required | 170 | 0.17 | −9 | 1.8 | Good |
| 40 | BCA | Vanillin | 10 | Kolliphor® HS15 + Brij® 35 | 8.0% DSPE-PEG(2000)-DBCO, 0.3% NR668 and Miglyol® 812 | Yes | 178 | 0.21 | −16 | 1.75 | Good |
| 41 | OCA | Vanillin | 5 | Kolliphor® HS15 + Brij® 35 | 2% PP9 and Miglyol® 812 | Yes | 174 | 0.26 | −2.6 | 6.9 | Okay |
| 42 | EBCA | vanillin | 4.5 | Kolliphor® HS15 + Pluronic® F68 | 18.6% cabazitaxel, 0.22% NR668 and 2.3% Miglyol® 812 | Yes | 175 | 0.22 | −3.1 | 1.19 | Okay |
| 43 | EBCA | vanillin | 4.6 | Kolliphor® HS15 + Pluronic® F68 | 23% cabazitaxel, 0.24% Lipid 780, and 3% Miglyol® 312 | Yes | 118 | 0.18 | −2 | 1.05 | Okay |
| 44 | EBCA | vanillin | 2.3 | Kolliphor® HS15 + Brij® L23 | 10.2% cabazitaxel and 2.3% Miglyol® 812 | Not required | 163 | 0.14 | −2.8 | 10.5 | Good |

The invention claimed is:

1. A nanoparticle comprising a poly(alkyl cyanoacrylate) homopolymer, or copolymer, at least one active agent and an anionic and radical inhibitor, wherein
the anionic and radical inhibitor is a compound having the following formula:

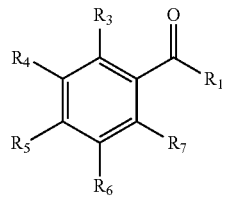

wherein
$R_1$ is H; and
$R_3$, $R_4$, $R_5$, $R_6$ and $R_7$ are independently selected from the group consisting of —H, —OH, $C_1$-$C_6$ alkoxide, $C_1$-$C_6$ alkyl, halides, carboxylic acid, ketone and aldehyde; wherein the anionic and radical inhibitor is present in an amount of 0.001 to 15 wt %, based on the weight of the nanoparticle.

2. The nanoparticle according to claim 1, wherein the active agent is a compound having a functional group selected from the group consisting of M-$NH_3$ (wherein M is a metal), R—$NH_2$, $R_1R_2$—NH, $R_1R_2R_3$N, $R_1$=$NR_2$, R—OH, R—Cl, R—Br, R—I, R—SH, $R_1$N=$NR_2$, R—NHOH, structurally associated $H_2O$, and enols.

3. The product of the process according to claim 1.

4. A process for the preparation of nanoparticles of a poly(alkyl cyanoacrylate) homopolymer or copolymer, comprising, in a single step, the anionic polymerisation of an oil-in-water miniemulsion, wherein said miniemulsion comprises
(i) at least one alkyl cyanoacrylate monomer;
(ii) at least one surfactant;
(iii) one or more active agents;
(iv) optionally an anionic polymerisation initiator; and
(v) an anionic and radical inhibitor, wherein the anionic and radical inhibitor is a compound having the following formula:

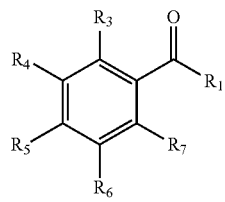

wherein
$R_1$ is H; and
$R_3$, $R_4$, $R_5$, $R_6$ and $R_7$ are independently selected from the group consisting of —H, —OH, $C_1$-$C_6$ alkoxide, $C_1$-$C_6$ alkyl, halides, carboxylic acid, ketone and aldehyde.

5. The process according to claim 4, wherein the anionic and radical inhibitor is a single compound which reacts reach with any of a nucleophile and a radical.

6. The process according to claim 4, wherein the anionic and radical inhibitor is present in an amount of 0.001 to 15 wt % of an oil phase of the miniemulsion.

7. The process according to claim 4, wherein the anionic and radical inhibitor has a higher affinity for radicals and nucleophiles than the at least one alkyl cyanoacrylate monomer.

8. The process according to claim 4, wherein the anionic and radical inhibitor has an octanol-water partition coefficient (log P) in the range of 1.0-3.0.

9. The process according to claim 4, wherein the anionic and radical inhibitor is selected from the group consisting of 4-hydroxy-3,5-dimethylbenzaldehyde, 4-hydroxy-3,5-dimethoxybenzaldehyde, vanillin, salicylaldehyde and benzaldehyde.

10. The process according to claim 4, wherein the active agent is a therapeutic agent or an imaging agent.

11. The process according to claim 4, wherein the at least one surfactant is at least one polyalkylene glycol selected from the group consisting of polyethylene glycols (PEG), polypropylene glycols (PPG), and mixtures thereof.

12. The process according to claim 4, wherein the at least one surfactant initiates the anionic polymerisation reaction.

13. The process according to claim 4, wherein the at least one surfactant in step (ii) comprises at least two polyalkylene glycols selected from the group consisting of polyethylene glycols (PEG), polypropylene glycols (PPG), and mixtures thereof.

14. The process according to claim 4, wherein the active agent comprises a functional group selected from the group consisting of M-$NH_3$ (wherein M is a metal), R—$NH_2$, $R_1R_2$—NH, $R_1R_2R_3$N, $R_1$=$NR_2$, R—OH, R—Cl, R—Br, R—I, R—SH, $R_1$N=$NR_2$, R—NHOH, structurally associated $H_2O$, and enols.

15. A pharmaceutical composition comprising the nanoparticle as defined in claim 1 and one or more pharmaceutically acceptable carriers, diluents or excipients.

16. A method of drug delivery or molecular imaging comprising administering the nanoparticle of claim 1.

17. A method of agriculture, aquaculture, antibacterial applications, nutraceuticals, food/feed applications, cosmetics, self-healing, household applications, or body care comprising administering or applying the nanoparticle of claim 1.

* * * * *